(12) United States Patent
Vermeer

(10) Patent No.: US 8,003,075 B2
(45) Date of Patent: *Aug. 23, 2011

(54) DIAGNOSTIC ASSAY FOR HUMAN MATRIX GLA-PROTEIN AND ITS USE AS A BIOMARKER

(75) Inventor: Cees Vermeer, Maastricht (NL)

(73) Assignee: MGP Diagnostics A/S, Mjondalen (NO)

( * ) Notice: Subject to any disclaimer, the term of this patent is extended or adjusted under 35 U.S.C. 154(b) by 0 days.

This patent is subject to a terminal disclaimer.

(21) Appl. No.: 12/763,474

(22) Filed: Apr. 20, 2010

(65) Prior Publication Data

US 2010/0323455 A1     Dec. 23, 2010

Related U.S. Application Data

(63) Continuation of application No. 10/832,734, filed on Apr. 26, 2004, now Pat. No. 7,700,296, which is a continuation-in-part of application No. 10/030,031, filed on Jan. 3, 2002, now Pat. No. 6,746,847, which is a continuation-in-part of application No. PCT/EP00/06173, filed on Jul. 2, 2000.

(30) Foreign Application Priority Data

Jul. 4, 1999   (EP) ..................................... 99202176
Mar. 23, 2000  (EP) ..................................... 00106409

(51) Int. Cl.
    *G01N 33/53* (2006.01)
(52) U.S. Cl. .......................... 424/1.13; 435/7.1; 435/7.2
(58) Field of Classification Search .................. None
See application file for complete search history.

(56) References Cited

U.S. PATENT DOCUMENTS 5,476,779 A    12/1995    Chen et al.

FOREIGN PATENT DOCUMENTS

WO    WO 01/02963 A1    1/2001
WO    WO 2005/046455 A2    5/2005

OTHER PUBLICATIONS

Teo et al. American J. of Neuroadiology 1997, vol. 18, p. 576-579.
Harlow et al. "Antibodies a Laboratory Manual," Cold Spring Harbor, NY, Cold Spring Harbor Laboratory Press, 1998, p. 141-155.
Schurgers et al. Z Kardiol. 2001 Suppl. 3, p. 111/57.
Shanahan et al. J. Clin. Invest. 1994 vol. 93, p. 2393-2402.
Search Report, European Patent Office, for EP 0 05 07 5994, dated Sep. 29, 2005 (4 pages).
Rutsch, F. and Terkeltaub, M.D. (2003) Parallels bweteen arterial and cartilage calcification: what understandign artery caliciﬁcation can teach us about chondrocalcosis Current Opinion in Rheumatology 15:302-310.
Spronk, H.M.H., Soute, B.A.M., Schurgers. L.J., Cleutjens, J.P.M., Thijssen, H.H.W., Demey, J.G.R., and Vermeer, C. (2001) Matrix Gla Protein Accumulates at the Border of Regions of Caliciﬁcation and Normal Tissue in the Media of the Arterial Vessel Wall, Biochem. Biophys. Res. Commun. 298:485-490.
Price et al. (1983) Matrix GLA Protein, A New ?-Carboxyglutamic Acid-Containing Protein Which is Associated with the Organic Matrix of Bone, Biochemical and Biophysical Research Communications 117:765-771.
Otawara et al. (1986) Developmental Appearance of Matrix GLA Protein During Cicification in the Rat, J. Biol. Chem. 261:10828-32.
Fraser et al. (1988) Lung, Heart, and Kidney Express High Levels of mRNA for the Vitamin K-dependent Matrix Gla Protein, Journal of Biological Chemistry 263:11033-11036.
Hauschka et al. (1989) Osteocalcin and Matrix Gla Protein: Vitamin K-Dependent Proteins in Bone, Physiological Reviews vol. 69 No. 3:990-1047.
Shearer, M.J. (1990) Annotation, British Journal of Haematology 75:156-162.
Vermeer, C. (1990) ?-Carboxyglutamate-Containing Proteins and the Vitamin K-Dependent Carboxylase, Biochem. J. 266:625-636.
Sadowski et al. (1991) Production of Polyclonal Antibodies to a Vitamin K-Dependent Epitope of Bone Matrix GLA Protein (MGP) by Synthetic Peptides, FASEB Journal 5:A944.
Hale et al. (1991) Carboxyl-Terminal Proteolytic Processing of Matrix Gla Protein, Journal of Biological Chemistry 266:21145-21149.
Loeser et al. (1992) Artluclar-Cartilage Matrix ?-Carboxyglutamic Acid-Containing Protein, Biochem. J. 282:1-6.
Luo et al. (1997) Spontaneous Calcification of Arteries and Cartilage in Mice Lacking Matrix GLA Protein, Nature 386:78-81.
Proudfoot et al. (1988) Vascular Calcification: New Insights Into an Old Problem, Journal of Pathology 185:1-3.
Proudfoot et al. (1998) Calsification of Human Vascular Cells In Vitro is correlated with High Levels of Matrix GLA Protein and Low Levels of Osteopontin Expression, Arterioscler Trhomb. Vasc. Biol. 18:379-388.
Shanahan et al. (1998) The Role of Gla Proteins in Vascular Calcification, Critical Reviews in Eukaryotic Gene Expression 8 (3&4):357-375.
Price et al, (1998) Warfarin Causes Rapid Calcification of the Elastic Lamellae in Rat Arteries and Heart Valves, Arteriosclerosis Thrombosis and Vascular Biology, 18:1400-1407.

(Continued)

*Primary Examiner* — Jacob Cheu
(74) *Attorney, Agent, or Firm* — Kalow & Springut LLP; William D. Schmidt

(57) ABSTRACT

The present invention includes a diagnostic assay for the detection and determination of MGP in a human serum sample, which comprises the use of one or more antibodies, preferably monoclonal antibodies, specifically recognizing epitopes on and/or conformations of human Matrix Gla-Protein. A method is provided for using MGP-related antigens as biomarkers for certain diseases, for example, atherosclerosis and other vascular diseases, and angiogenesis/neogenesis in tumor development. Monoclonal antibodies of class IgG are described for use in the assay, which are defined herein as mAb3-15, mAb35-49[Glu], mAb35-49[Gla], mAb35-53 [Glu], and mAb35-53[Gla]. Polyclonal antibodies and methods are also disclosed for measuring MGP in a human serum sample.

5 Claims, 14 Drawing Sheets

OTHER PUBLICATIONS

Dhore et al. (1999) Osteocalcin and Matrix GLA Protein Deposition is Enhanced in Human Atherosclerotic Plaques, FASEB Journal, 13:A204.

Braam et al. (2000) Assay for Human Matrix GLA Protein In Serium: Potential Applications In the Cardiovascular Field, Arteriosclerosis Thrombosis and Vascular Biology, 20:1257-61.

Campbell Alisa M. (section 1.3.4. p. 29; Monoclonal Antibody Technology (1984) Elsevier Science Publishers).

Kiefer et al. (1988) The cDNA and derived amino acid sequence for human and bovine matrix Gla protein. Nucleic Acids Res. 16: 5213.

Watson et al. Recombinant DNA, second edition (1996) Ch. 12, Transferring Genes into Mammalian Cells, pp. 217-230.

```
MetArgGlySerHisHisHisHisHisHisGlySerGlyIleMetValArgProLeuAsnSerIle
ATGAGAGGATCGCATCACCATCACCATCACGGATCCGGCATCATGGTTCGACCATTGAACTCGATC
         - 6His tag ------

ValAlaValSerGlnAsnMetGlyIleGlyLysAsnGlyAspLeuProTrpProProLeuArgAsn
GTCGCCGTGTCCCAAAATATGGGGATTGGCAAGAACGGAGACCTACCCTGGCCTCCGCTCAGGAAC

GluPheLysTyrPheGlnArgMetThrThrThrSerSerValGluGlyLysGlnAsnLeuValIle
GAGTTCAAGTACTTCCAAAGAATGACCACAACCTCTTCAGTGGAAGGTAAACAGAATCTGGTGATT

MetGlyArgLysThrTrpPheSerIleProGluLysAsnArgProLeuLysAspArgIleAsnIle
ATGGGTAGGAAAACCTGGTTCTCCATTCCTGAGAAGAATCGACCTTTAAAGGACAGAATTAATATA

ValLeuSerArgGluLeuLysGluProProArgGlyAlaHisPheLeuAlaLysSerLeuAspAsp
GTTCTCAGTAGAGAACTCAAAGAACCACCACGAGGAGCTCATTTTCTTGCCAAAAGTTTGGATGAT

AlaLeuArgLeuIleGluGlnProGluLeuAlaSerLysValAspMetValTrpIleValGlyGly
GCCTTAAGACTTATTGAACAACCGGAATTGGCAAGTAAAGTAGACATGGTTTGGATAGTCGGAGGC

SerSerValTyrGlnGluAlaMetAsnGlnProGlyHisLeuArgLeuPheValThrArgIleMet
AGTTCTGTTTACCAGGAAGCCATGAATCAACCAGGCCACCTTAGACTCTTTGTGACAAGGATCATG

GlnGluPheGluSerAspThrPhePheProGluIleAspLeuGlyLysTyrLysLeuLeuProGlu
CAGGAATTTGAAAGTGACACGTTTTTCCCAGAAATTGATTTGGGGAAATATAAACTTCTCCCAGAA

TyrProGlyValLeuSerGluValGlnGluGluLysGlyIleLysTyrLysPheGluValTyrGlu
TACCCAGGCGTCCTCTCTGAGGTCCAGGAGGAAAAAGGCATCAAGTATAAGTTTGAAGTCTACGAG

LysLysGlySerArgSerAlaCysIleGluGlyArgTyrGluSerHisGluSerMetGluSerTyr
AAGAAAGGTTCCAGATCTGCATGCATTGAAGGTCGTTATGAATCACATGAAAGCATGGAATCTTAT
                 SphI  - Xa site  -< Matrix Gla protein GluLeuAsnProPheIleAsnArgArgAsnAlaAsnThrPheIleSerProGlnGlnArgTrpArg
GAACTTAATCCCTTCATTAACAGGAGAAATGCAAATACCTTCATATCCCCTCAGCAGAGATGGAGA AlaLysValGlnGluArgIleArgGluArgSerLysProValHisGluLeuAsnArgGluAlaCys
GCTAAAGTCCAAGAGAGGATCCGAGAACGCTCTAAGCCTGTCCACGAGCTCAATAGGGAAGCCTGT AspAspTyrArgLeuCysGluArgTyrAlaMetValTyrGlyTyrAsnAlaAlaTyrAsnArgTyr
GATGACTACAGACTTTGCGAACGCTACGCCATGGTTTATGGATACAATGCTGCCTATAATCGCTAC PheArgLysArgArgGlyAlaLysLysLeuAsn
TTCAGGAAGCGCCGAGGGGCCAAAAAGCTTAAT
                       > HindIII
```

Figure 1

DIAGNOSTIC ASSAY FOR HUMAN MATRIX GLA-PROTEIN AND ITS USE AS A BIOMARKER

This application is a continuation application of U.S. patent application Ser. No. 10/832,734 filed on Apr. 26, 2004, which is a continuation-in-part of U.S. patent application Ser. No. 10/030,031, filed on Jan. 3, 2002, the entire disclosures of which are incorporated by reference herein.

FIELD OF THE INVENTION

The present invention is in the field of molecular biology and diagnostics. In particular, the invention relates to a diagnostic assay for human Matrix Gla-protein (MGP), and its use as a biomarker for vascular conditions and vascular new formation.

BACKGROUND OF THE INVENTION

Cardiovascular disease is one of the major life-threatening diseases in Western society, but biomarkers to monitor the severity or the progression of the disease are presently not available. Also, the number of biochemically detectable risk factors (e.g., serum cholesterol, triglycerides, ApoE genotype) is surprisingly low.

Vitamin K is a cofactor in the posttranslational conversion of glutamate residues into γ-carboxyglutamate (Gla). At this time, 10 mammalian Gla-containing proteins have been described in detail, and the number of Gla-residues per molecule varies from 3 (osteocalcin) to 13 (protein Z). In all cases in which their function was known, the activity of the various Gla-proteins was strictly dependent on the presence of the Gla-residues (Shearer, M. J., *Brit. J. Haematol.* (1990) 75:156-162; Vermeer, C., *Biochem. J.* (1990) 266:626-636). Gla-proteins are synthesized in various tissues, for instance the liver, bone and vessel wall. Blood coagulation factors II (prothrombin), VII, IX and X are examples of Gla-proteins synthesized in the liver, examples of so-called extrahepatic Gla-proteins are osteocalcin and Matrix Gla-Protein (Hauschka, P. V. et al., *Phys. Rev.* (1989) 69:990-1047).

Matrix Gla-Protein is a vitamin K-dependent protein synthesized in bone and in a number of soft tissues including heart and vessel wall. In experimental animals its soft tissue expression is high immediately after birth, but decreases in the months thereafter. Only in cartilage and arteries does its expression seem to continue lifelong. Although the precise function of MGP on a molecular level has remained unknown so far, experiments with MGP-deficient transgenic animals ("knock-out" mice) have shown that MGP has a prominent role in the prevention of vascular mineralization: MGP-deficient animals are born to term but develop severe aortic calcification (as analyzed by X-ray) in the first weeks of life; and eventually all animals die within 6-8 weeks after birth due to rupture of the aorta or one of the other main arteries (Luo, G. et al., *Nature* (1997) 386:78-81).

MGP contains five Gla-residues which are essential for its calcification-inhibitory function. This was discovered by Price et al., who treated rats with the vitamin K-antagonist warfarin thus blocking the formation of Gla-residues (Price, P. A. et al. *Arterioscler. Thromb. Vasc. Biol.* (1998) 18: 1400-1407). The treatment protocol induced vitamin K-deficiency in the vasculature and lead to vascular calcification within 3 weeks. Hence an inadequate vitamin K-status leading to incomplete MGP carboxylation is a risk factor for cardiovascular calcification. Conformation-specific antibodies recognizing either carboxylated (=active conformation containing 5 Gla-residues/mol) or under-carboxylated (=inactive conformation containing less than 5 Gla-residues/mol) are a powerful tool in the diagnostics of cardiovascular disease.

MGP was discovered in bone (Price, P. A. et al., *Biochem. Biophys. Res. Commun.* (1983) 117:765-771), but in situ hybridization experiments showed that it is also expressed in other tissues including the vessel wall (Fraser, D. J. et al., *J. Biol. Chem.* (1988) 263:11033-11036). With polyclonal antibodies raised against a synthetic peptide homologous to the C-terminus of bovine MGP, the protein was also found in cartilage via immunohistochemical staining (Loeser, R. F. et al., *Biochem. J.* (1992) 282:1-6). A radioimmunoassay was developed for the detection of serum MGP in the rat, but in these experiments circulating MGP was correlated with maturation of rat bone, and not with vascular biology (Otawara, Y. et al., *J. Biol. Chem.* (1986) 261:10828-10832).

Research concerning the role of MGP in the vessel wall has not started before the discovery by Luo et al. (supra) that MGP is a strong inhibitor of vascular calcification in mice. Since then, evidence has accumulated suggesting that bone calcification and atherosclerotic vessel wall calcification proceed via very similar mechanisms, in which the same proteins (including MGP) are used, (Proudfoot, D. et al., *Arterioscler. Thromb. Vasc. Biol.* (1998) 18:379-388; Proudfoot, D. et al., *J. Pathol.* (1998) 185:1-3). Most studies on the regulation of MGP expression have been performed in smooth muscle cell cultures, with mRNA detection as a measure for MGP synthesis. Recent studies in humans have shown that, although MGP mRNA is constitutively expressed by normal vascular smooth muscle cells, it is substantially upregulated in cells adjacent to both medial and intimal calcification (Shanahan, C. M. et al., *Crit. Rev. in Eukar. Gene Expr.* (1998) 8:357-375).

The prior art neither teaches nor suggests the use of MGP as a marker for angiogenesis or cardiovascular disease, or the like, nor does it disclose an assay for circulating MGP in humans.

As stated above, biomarkers to monitor the severity or the progression of cardiovascular disease are not available up till now, and the number of biochemically detectable risk factors is very low. Therefore, there is clearly a need for biomarkers for vascular characteristics, for assessment of the severity or progression of atherosclerosis and related diseases, as well as for monitoring the effect of treatment during vascular disease.

SUMMARY OF THE INVENTION

In accordance with an aspect of the present invention, a diagnostic assay, preferably immunoassay, is provided for the detection and determination of MGP in a human serum sample, which comprises the use of one or more antibodies, in particular monoclonal antibodies, specifically recognizing epitopes on and/or conformations of human Matrix Gla-Protein (human MGP).

The invention further includes a method for the production of such antibodies.

In another aspect of the invention, a method is included for the production of chimeric recombinant MGP constructs which are recognized by said antibodies.

In yet another aspect of the invention, an assay is included wherein said antibodies and said chimeric recombinant MGP constructs recognized by said antibodies are used, allowing the detection of MGP, either (a) the total immunoreactive antigen, carboxylated, or (b) the fraction of carboxylated (=5 Gla-residues/mol), or (c) the fraction of undercarboxylated MGP ($\leq$4 Gla-residues/mol), in human serum.

In still a further aspect of the invention, a method is included for using MGP-related antigens as biomarkers for certain diseases, for example, atherosclerosis and other vascular diseases, and angiogenesis/neogenesis in tumor development, and diseases of the cartilage, such as osteoarthritis, Bechterew's disease, and rheumatoid arthritis.

In a preferred embodiment of the invention, monoclonal antibodies of class IgG are included for use in said diagnostic immunoassay which are obtainable by hybridomas formed by fusion of cells from a mouse myeloma and spleen cells from a mouse previously immunized with a peptide homologous to certain human MGP residues, in particular one of human MGP residues 3-15, human MGP residues 35-49, human MGP residues 35-53, human MGP residues 54-84, and human MGP residues 61-79, which antibodies are also referred to herein as mAb3-15, mAb35-49, mAb35-53, mAb54-84, and mAb61-79, respectively. Of these, mAb3-15, mAb35-49, and mAb35-53 are preferred antibodies. Of these, mAb61-79 and mAb54-84 can be used for detecting MGP without regard to its state of posttranslational modification. Peptides of residues 35-49 are used in two different conformations: those containing glutamic acid at positions 37, 41, and 48 and those containing Gla at those positions. Peptides of residues 35-53 are also used in two different conformations: those containing glutamic acid at positions 37, 41, 48, and 52 and those containing Gla at those positions. These peptides are designated as 35-49[Glu], 35-49[Gla], 35-53[Glu], and 35-53[Gla], respectively.

The present invention includes cell lines producing monoclonal antibodies specific for human MGP, conformations of human MGP, and regions of human MGP, methods of making cell lines that produce antibodies specific for human MGP, conformations of human MGP, and regions of human MGP, monoclonal antibodies specific for human MGP, conformations of human MGP, and regions of human MGP, diagnostic assays for human MGP, and kits for assaying or detecting human MGP, conformations of human MGP, and fragments of human MGP.

The present invention includes a method of detecting one or more diseases or disorders of the human vascular system, or diseases or disorders of human cartilage, comprising exposing a human serum sample to a monoclonal antibody capable of recognizing an epitope of human MGP.

The present invention also includes a method for detecting one or more diseases or disorders of the human vascular system, or diseases or disorders of human cartilage, comprising exposing a human serum sample to a polyclonal antibody capable of recognizing an epitope of human MGP.

These and other aspects of the present invention will be more fully outlined in the detailed description which follows.

BRIEF DESCRIPTION OF THE DRAWINGS

FIG. 1 represents the assessed DNA nucleotide sequence and its derived amino acid sequence of insert, e.g., MGP linked to murine dihydrofolate reductase ("DHFR") and equipped with a N-terminal 6-His tag. The "Xa site" indicates a linker of -Ile-Glu-Gly-Arg- which is sensitive to proteolytic cleavage by clotting factor Xa. See also SEQ ID NOS: 1 and 2.

FIG. 12 illustrates the antigen-capture technique: triplicate measurements of the standard reference curve were prepared on three consecutive days. Unknown plasma or serum samples can be read from the curve. In this technique, a labeled tracer peptide ($MGP^{3-15}$) was added to the serum, whereas monoclonal antibodies (mAb3-15) were coated onto the microtiter plate. The apparent MGP concentrations in the test sample are based on the assumption that the affinities of tracer and native MGP for the antibody are similar.

DETAILED DESCRIPTION OF THE PREFERRED EMBODIMENTS

Figure 2:
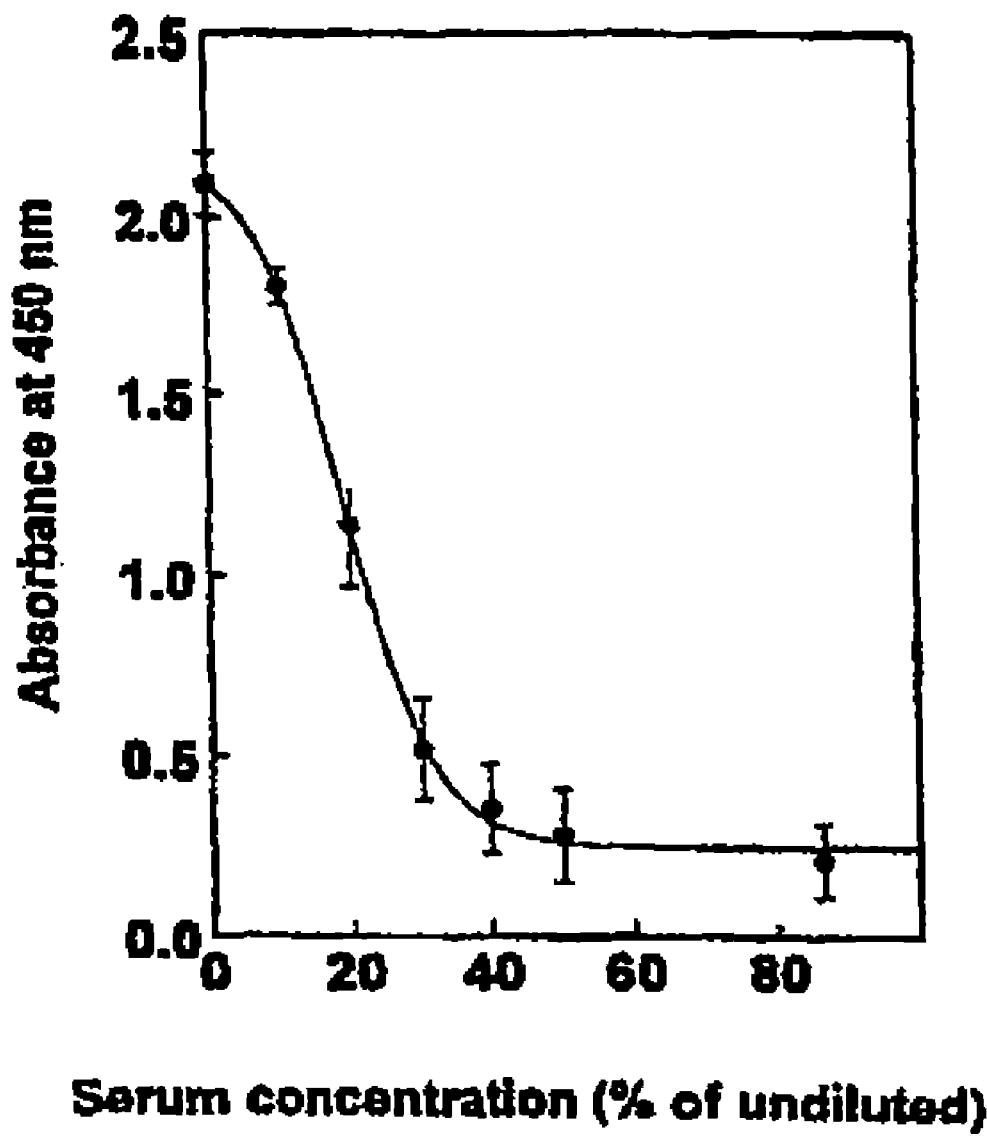
FIG. 2 shows a dose-response reference curve for MGP in human reference serum. Points are means of duplicate measurements made on 12 different days; error bars represent standard deviation.

The present invention is based on the surprising discovery that the vitamin K-dependent matrix Gla-protein, MGP, appears to play a key role in preventing vascular calcification. MGP is synthesized in a vitamin K-dependent way in smooth muscle cells of the healthy vessel wall and its mRNA transcription is substantially upregulated in atherosclerotic lesions.

MGP is a protein that contains five glutamate residues, which may be modified by the addition of an extra carboxyl group. Whereas unmodified glutamate is abbreviated as Glu, carboxylated glutamate is designated as Gla. Gla residues are formed in a reaction in which vitamin K acts as a coenzyme. Human MGP contains 84 amino acid residues, with Gla residues at positions 2, 37, 41, 48, and 52 (Kiefer et al. (1988) Nucleic Acids Res. 16:5213). The Gla residue at position 2 is not regarded as part of human MGP's "Gla-domain," because it is atypically located. Thus, the Gla domain in human MGP may contain four Gla residues. The Gla-residues in MGP are an absolute requirement for its biological activity.

A typically Western type of diet contains insufficient vitamin K to fully carboxylate all Glu residues in MGP into Gla residues. As a consequence, non-carboxylated species of MGP are formed in a normal, "healthy" human population. These non-carboxylated, or under-carboxylated, species have no biological activity. The normal biological activity of MGP is inhibition of vascular calcification.

Inhibition of vascular calcification is an important factor in mediating the development and progression of cardiovascular diseases and disorders. At least two MGP-associated risk factors exist for cardiovascular disease. The risk factors are (1) low constitutive expression of MGP, in any of its forms (active or inactive), and (2) poor, under- or non-carboxylation of MGP, which can lead to a lessened ability of MGP to inhibit the calcification process.

The present invention includes cell lines producing monoclonal antibodies specific for human MGP and regions of human MGP, methods of making cell lines that produce antibodies specific for human MGP and conformations of human MGP, monoclonal antibodies specific for human MGP and conformations of human MGP, diagnostic assays for human MGP, and kits for assaying or detecting human MGP and conformations of human MGP. In this context "conformations of MGP" refers to MGP species containing or lacking posttranslationally modified amino acid residues. The methods and compositions of the present invention are particularly useful for detecting or monitoring diseases or disorders of the human vascular system and diseases or disorders of human cartilage.

In certain embodiments, the present invention includes cell lines producing monoclonal antibodies from a mouse previously immunized with a peptide homologous to certain human MGP residues, in particular human MGP residues 3-15, human MGP residues 35-49[Glu], human MGP residues 35-49[Gla], human MGP residues 35-53[Glu], human MGP residues 35-53[Gla], human MGP residues 54-84, and human MGP residues 61-79, which antibodies are also referred to herein as mAb3-15, mAb35-49[Glu], mAb35-49[Gla], mAb35-53[Glu], mAb35-53[Gla], mAb54-84, and mAb61-79, respectively. Of these, mAb3-15, mAb35-49[Glu] and mAb35-53[Glu] are preferred antibodies for detecting MGP lacking posttranslational modifications. Of these, mAb61-79 and mAb54-84 are preferred for detecting MGP without regard to its state of posttranslational modification. Methods of making the cell lines are included, monoclonal antibodies produced by the cells are included, and kits for assaying or detecting human MGP comprising the antibodies are included. The monoclonal antibodies mAb3-15, mAb61-79, and mAb54-84 allow for identification of human MGP without regard to human MGP's carboxylation state. The remainder of the antibodies are directed to regions that include glutamines that can be carboxylated. Thus, the present invention allows for characterization of human MGP in carboxylated forms and in uncarboxylated forms, as well as without regard to state of postranslational modification.

In another embodiment, the present invention includes a diagnostic kit for assaying human matrix Gla protein in a serum sample, comprising: one or more monoclonal antibodies directed against an epitope in human matrix Gla protein residues 3-15, 35-49[Glu], 35-49[Gla], 35-53[Glu], 35-53[Gla], alone or in combination with a monoclonal antibody directed against an epitope in human matrix Gla protein residues 54-84, or combinations thereof, wherein said one or more antibodies are produced by a hydridoma formed by fusion of cells from a mouse myeloma and spleen cells from a mouse previously immunized with a peptide homologous to human matrix Gla protein residues 3-15, 35-49[Glu], 35-49[Gla], 35-53[Glu], 35-53[Gla], 61-79, or 54-84.

In another embodiment, the present invention includes a method for determining matrix Gla protein present in a human serum sample, comprising: obtaining a human serum sample; exposing the human serum sample to one or more monoclonal antibodies that specifically recognizes an epitope on human matrix Gla protein residues 3-15, 35-49[Glu], 35-49[Gla], 35-53[Glu], 35-53[Gla] alone or in combination with a monoclonal antibody that specifically recognizes an epitope in human matrix Gla protein residues 61-79, or 54-84, or a combination thereof, the one or more monoclonal antibodies being present in a predetermined amount so that a portion of the one or more monoclonal antibodies remain uncomplexed to the human matrix Gla protein present in the sample; and measuring the amount of uncomplexed one or more monoclonal antibodies so as to determine the matrix Gla protein in the human serum sample.

In another embodiment, the present invention includes processes for monitoring or detecting a disease, comprising: exposing a human serum sample to a monoclonal antibody of class IgG, comprising a monoclonal antibody directed against an epitope in human matrix Gla protein residues 3-15, 35-49[Glu], 35-49[Gla], 35-53[Glu], or 35-53[Gla], alone or in combination with a monoclonal antibody directed against an epitope in human matrix Gla protein residues 61-79, or 54-84, or a combination thereof, wherein said antibody is produced by a hydridoma formed by fusion of cells from a mouse myeloma and spleen cells from a mouse previously immunized with a peptide homologous to human matrix Gla protein residues 3-15, 35-49[Glu], 35-49[Gla], 35-53[Glu], or 35-53[Gla], or 61-79 or 54-84, and detecting a level of human matrix Gla protein in said serum sample using the monoclonal antibody, or a combination thereof, wherein an higher or lower level of human matrix Gla protein in said serum sample is associated with a disease, including, for example, coronary atherosclerosis, vascular calcification, angiogenesis, a disease of the vascular system, diabetes mellitus, ectopic calcification in tumor development, or diseases or disorders of human cartilage, including, for example, osteoarthritis, Bechterew's disease, and rheumatoid arthritis, thereby monitoring or detecting coronary atherosclerosis, vascular calcification, angiogenesis, a disease of the vascular system, diabetes mellitus, ectopic calcification in tumor development, or diseases or disorders of human cartilage.

In another embodiment, the present invention includes a monoclonal antibody of class IgG, comprising a monoclonal antibody directed against an epitope in human matrix Gla protein residues 3-15, wherein said antibody is produced by a hydridoma formed by fusion of cells from a mouse myeloma and spleen cells from a mouse previously immunized with a peptide homologous to human matrix Gla protein residues 3-15.

In another embodiment, the present invention includes a monoclonal antibody of class IgG, comprising a monoclonal antibody directed against an epitope in human matrix Gla protein residues 35-49[Glu], wherein said antibody is produced by a hydridoma formed by fusion of cells from a mouse myeloma and spleen cells from a mouse previously immunized with a peptide homologous to human matrix Gla protein residues 35-49[Glu].

In another embodiment, the present invention includes a monoclonal antibody of class IgG, comprising a monoclonal antibody directed against an epitope in human matrix Gla protein residues 35-49[Gla], wherein said antibody is produced by a hydridoma formed by fusion of cells from a mouse myeloma and spleen cells from a mouse previously immunized with a peptide homologous to human matrix Gla protein residues 35-49[Gla].

In another embodiment, the present invention includes a monoclonal antibody of class IgG, comprising a monoclonal antibody directed against an epitope in human matrix Gla protein residues 35-53[Glu], wherein said antibody is produced by a hydridoma formed by fusion of cells from a mouse myeloma and spleen cells from a mouse previously immunized with a peptide homologous to human matrix Gla protein residues 35-53[Glu].

In another embodiment, the present invention includes a monoclonal antibody of class IgG, comprising a monoclonal antibody directed against an epitope in human matrix Gla protein residues 35-53[Gla], wherein said antibody is produced by a hydridoma formed by fusion of cells from a mouse myeloma and spleen cells from a mouse previously immunized with a peptide homologous to human matrix Gla protein residues 35-53[Gla].

In another embodiment, the present invention includes a monoclonal antibody of class IgG, comprising a monoclonal antibody directed against an epitope in human matrix Gla protein residues 61-79, wherein said antibody is produced by a hydridoma formed by fusion of cells from a mouse myeloma and spleen cells from a mouse previously immunized with a peptide homologous to human matrix Gla protein residues 61-79.

In another embodiment, the present invention includes a monoclonal antibody of class IgG, comprising a monoclonal antibody directed against an epitope in human matrix Gla protein residues 54-84, wherein said antibody is produced by a hydridoma formed by fusion of cells from a mouse myeloma and spleen cells from a mouse previously immunized with a peptide homologous to human matrix Gla protein residues 54-84.

In another embodiment, the present invention includes a hybridoma cell line B11A#1 deposited with Deutsche Sammlung von Mikroorganizmen und Zellkulturen GmbH (DSMZ) as accession number DSM ACC2639.

In another embodiment, the present invention includes a hybridoma cell line 52.1#1 deposited with Deutsche Sammlung von Mikroorganizmen und Zellkulturen GmbH (DSMZ) as accession number DSM ACC2638.

In another embodiment, the present invention includes a diagnostic assay for the detection and determination of MGP in a human serum sample, which comprises the use of one or more antibodies specifically recognizing epitopes on and/or conformations of human Matrix Gla-Protein. In a preferred embodiment, the assay is an immunoassay. In any of these embodiments, the antibodies can be monoclonal antibodies. The diagnostic assay can employ one or more of mAb3-15, mAb35-49[Glu], mAb35-49[Gla], 35-53[Glu], and 35-53 [Gla], alone or in combination with mAb61-79, or 54-84.

In another embodiment, the present invention includes a chimeric recombinant MGB construct, comprising a chimeric recombinant MGB construct that is recognized by one or more of the antibodies of the aforementioned embodiments.

In another embodiment, the present invention includes one or more MGP conformations or MGP-related antigens, or one or more fragments of MGP, as biomarkers for one or more diseases. The invention also provides uses of total MGP, specific MGP conformations or an MGP-related antigen, or a fragment of MGP in monitoring a disease or disorder, wherein the disease or disorder is selected from atherosclerosis and other vascular diseases, angiogenesis/neogenesis in tumor development, and a disease or disorder of human cartilage. The disease or disorder of human cartilage includes, for example, osteoarthritis, Bechterew's disease, and rheumatoid arthritis.

In another embodiment, the present invention includes a monoclonal antibody of class IgG produced by a hybridoma formed by fusion of cells from a mouse myeloma and spleen cells from a mouse previously immunized with a peptide homologous to human MGP residues 3-15, which antibody is defined herein as mAb3-15.

In another embodiment, the present invention includes a monoclonal antibody of class IgG produced by a hybridoma formed by fusion of cells from a mouse myeloma and spleen cells from a mouse previously immunized with a peptide homologous to human MGP residues 35-49[Glu], which antibody is defined herein as mAb35-49[Glu].

In another embodiment, the present invention includes a monoclonal antibody of class IgG produced by a hybridoma formed by fusion of cells from a mouse myeloma and spleen cells from a mouse previously immunized with a peptide homologous to human MGP residues 35-49[Gla], which antibody is defined herein as mAb35-49[Gla].

In another embodiment, the present invention includes a monoclonal antibody of class IgG produced by a hybridoma formed by fusion of cells from a mouse myeloma and spleen cells from a mouse previously immunized with a peptide homologous to human MGP residues 35-53[Glu], which antibody is defined herein as mAb35-53[Glu].

In another embodiment, the present invention includes a monoclonal antibody of class IgG produced by a hybridoma formed by fusion of cells from a mouse myeloma and spleen cells from a mouse previously immunized with a peptide homologous to human MGP residues 35-53[Gla], which antibody is defined herein as mAb35-53[Gla].

In another embodiment, the present invention includes a monoclonal antibody of class IgG produced by a hybridoma formed by fusion of cells from a mouse myeloma and spleen cells from a mouse previously immunized with a peptide homologous to human MGP residues 61-79, which antibody is defined herein as mAb61-79.

In another embodiment, the present invention includes a monoclonal antibody of class IgG produced by a hybridoma formed by fusion of cells from a mouse myeloma and spleen cells from a mouse previously immunized with a peptide homologous to human MGP residues 54-84, which antibody is defined herein as mAb54-84.

In still another aspect of the invention, a kit is included, comprising a device suitable for carrying out the diagnostic assay according to the present invention, including one or more antibodies specifically recognizing epitopes on and/or conformations of human Matrix Gla-Protein, chemical agents useful or necessary to carry out the assay, which are familiar to the persons skilled in the art, and preferably instructions on how the assay is to be carried out in an optimal way.

One advantage of the present invention is the ability to fully characterize the carboxylation state of a sample of human MGP. In accordance with the present invention, this information will provide data as to risk of diseases or disorders including, but not limited to, diseases or disorders related to vascular calcification and diseases or disorders of human cartilage. The sample is subjected to analysis using the compositions and methods of the present invention in, for example, an immunoassay. Convenient immunoassays include, for example, enzyme linked immunosorbent assays (ELISAs), immunohistochemical techniques, and Western blots.

For those monoclonal antibodies generated using peptides that are not carboxylated, samples of human MGP with carboxylated residues will not bind with monoclonal antibodies generated using peptides that are not carboxylated. Thus, an indication that an antibody binds to MGP in a given sample comprising human MGP is indicative that the human MGP of the sample is not carboxylated at the residue corresponding to the particular monoclonal antibody (i.e., mAb3-15, mAb35-49[Glu], mAb35-53[Glu], mAb61-79, and mAb54-84). Similarly, for monoclonal antibodies that can be generated using peptides containing Gla-residues, samples of human MGP with non-carboxylated residues would not bind with monoclonal antibodies generated using peptides containing Gla-residues. In this case, an indication that an antibody binds to MGP in a given sample comprising human MGP is indicative that the human MGP of the sample is carboxylated at the residue corresponding to the particular monoclonal antibody (i.e., mAb35-49[Gla], mAb35-53[Gla]).

With this disclosure in hand, and by observing the reactivity pattern of a sample to the monoclonal antibodies of the present invention, a person of ordinary skill in the art can determine the ratio between carboxylated and under-carboxylated MGP, which is a determinant of the calcification inhibitory activity of MGP. In addition, ratios of reactivity of a sample to the aforementioned monoclonal antibodies to reactivity of the sample to mAb61-79 or mAb54-84 can be generated, providing even more information about the sample, for example, relative level of postranslational modification (e.g., carboxylation) with respect to total human MGP (as measured by mAb61-79 or mAb54-84, respectively). Ratios of reactivity can be determined using any method known in the art, for example, ELISA. For anti-MGP35-49[Glu] and anti-MGP35-53[Glu], less than 5% cross-reaction with carboxylated MGP is observed.

The methods and compositions of the present invention can also be used to monitor changes in the carboxylation status of human MGP. For example, a human sample can be assayed using the methods and compositions of the present invention to establish a baseline level of carboxylation of MGP in a human. A change in the carboxylation state of the human's MGP can then be determined following any therapy, drugs, protocols, or treatments known or suspected to affect vascular calcification, diseases related to vascular calcification, or level of carboxylation of human MGP.

The present invention also includes the use of serum MGP levels as a biomarker for one or more human diseases. In this regard, serum levels of MGP can be related to the occurrence, onset, progression, or regression of one or more diseases, as described herein. For example, the present disclosure describes the phenomenon that circulating MGP is correlated to cardiovascular calcification, coronary atherosclerosis, diabetes mellitus, malignancies, diseases or disorders of the cardiovascular system, and diseases or disorders of human cartilage, for example, osteoarthritis, Bechterew's disease, and rheumatoid arthritis. Serum levels of MGP can also be used to monitor efficacy of treatment regimens for the aforementioned diseases, or the efficacy of vitamin K administration therapies, vitamin K inhibitor therapies, or therapies affecting vitamin K metabolism. Serum levels of MGP can also be used to monitor the efficacy of dietary regimens aimed at increasing vitamin K levels. For example, serum levels of MGP can be used to identify groups in a mammal population, for example a human population, which might benefit most from vitamin K-enriched foods or vitamin K-enriched food supplements.

Accordingly, the present invention includes a method for detecting one or more diseases or disorders of the human vascular system or one or more diseases of human cartilage, comprising exposing a human serum sample to an antibody capable of recognizing an epitope of human MGP. The antibody can be a monoclonal antibody or a polyclonal antibody. Preferably, the antibody is a monoclonal antibody.

In one embodiment, the method for detecting one or more diseases or disorders of the human vascular system comprises exposing a human serum sample to an antibody capable of recognizing an epitope of human MGP, determining the level of MGP in the human serum sample, comparing the level of MGP in the human serum sample to a serum level of MGP in a human population sample, and determining whether the level of MGP in the human serum sample is higher or lower than the serum level of MGP in the human population sample. In one embodiment, the epitope of human MGP is found in the group consisting of human MGP residues 3-15, 35-49, 35-53, and 61-79. In another embodiment, the one or more diseases or disorders of the human vascular system is vascular calcification. In another embodiment, the one or more diseases or disorders of the human vascular system is coronary atherosclerosis. In another embodiment, the one or more diseases or disorders of the human vascular system is a vascularized neoplasm. Preferably, the vascularized neoplasm is a malignant tumor. In another embodiment, the one or more diseases of human cartilage includes osteoarthritis, Bechterew's disease, or rheumatoid arthritis. In another embodiment, the monoclonal antibody is capable of recognizing a carboxylated epitope on human MGP and the monoclonal antibody is incapable of recognizing a noncarboxylated epitope on human MGP. In yet another embodiment, the monoclonal antibody is capable of recognizing a noncarboxylated epitope on human MGP and the monoclonal antibody is incapable of recognizing a carboxylated epitope on human MGP. In yet another embodiment, the monoclonal antibody does not distinguish between carboxylated and non-carboxylated forms of human MGP.

In another embodiment, the present invention includes a method for detecting one or more diseases or disorders of the human vascular system, or one or more diseases or disorders of human cartilage, comprising exposing a human serum sample to a polyclonal antibody capable of recognizing an epitope of human MGP.

In another embodiment, the present invention includes a method for detecting one or more diseases or disorders of the human vascular system, or one or more diseases or disorders of human cartilage, comprising exposing a human serum sample to a polyclonal antibody capable of recognizing an epitope of human MGP, determining a level of MGP in the human serum sample, comparing the level of MGP in the human serum sample to a serum level of MGP in a human population sample, and determining whether the level of MPG in the human serum sample is higher or lower than the serum level of MGP in the human population sample. In one embodiment, the one or more diseases or disorders of the human vascular system is coronary atherosclerosis. The polyclonal antibody can be an antibody directed against MGP or a fragment thereof.

Upon exposure of a human serum sample to an antibody capable of recognizing human MGP, a level of MGP in the human serum sample can be determined, by any method known in the art, preferably using the compositions of the present invention. Once a level in the human serum sample is obtained, the level in the human serum sample can be compared to the average level of serum MGP in a human population. This human population can be selected by any suitable method known in the art, including a random sample of humans. The human population can be as small as a few persons, or as large as many thousands or persons. Preferably, the human population is large enough that, when compared with the human serum sample to be tested, the human population sample is capable of yielding a statistically significant difference between the human population sample and a serum sample of an individual with a disease or disorder of the vascular system or a disease or disorder of cartilage, for example, coronary atherosclerosis or rheumatoid arthritis, at the 95% or better confidence level.

In a preferred embodiment, the monoclonal antibody recognizes an epitope of human MGP found in the group consisting of human MGP residues 3-15, 35-49, 35-53, and 61-79. However, any monoclonal antibody capable of being employed in a human serum assay would suffice.

In a preferred embodiment, the one or more diseases or disorders of the human vascular system is coronary atherosclerosis. In another embodiment, the one or more diseases or disorders of the human vascular system is a vascularized neoplasm. The vascularized neoplasm can be, for example, a malignant tumor. In accordance with the disclosure herein, levels of serum MGP are elevated in patients with a vascularized neoplasm.

The monoclonal antibody employed to detect MGP in a human serum sample may be specific for a carboxylated epitope, specific for a noncarboxylated epitope, or incapable of distinguishing between a carboxylated and non-carboxylated epitope on MGP.

Preferably, the human population sample is substantially free of vascular disease or cartilage disease. By "substantially free of vascular disease or cartilage" is meant that at least 80% of the human population sample has not been diagnosed with a vascular disease or disorder or a disease of the cartilage. More preferably, at least 90% of the human population sample has not been diagnosed with a vascular disease or disorder or a disease of the cartilage. Most preferably, at least 99% of the human population sample has not been diagnosed with a vascular disease or disorder or a disease of the cartilage. The phrase "vascular disease or disorder" includes, for example, moderate to severe cardiovascular calcification, moderate to severe coronary atherosclerosis, type I diabetes mellitus, and neoplastic growths that are vascularized such as, for example, malignant tumors. The phrase "disease of the cartilage" includes, for example, moderate to severe osteoarthritis, Bechterew's disease, and moderate to severe rheumatoid arthritis. More preferably, less than 30% of the human population sample displays clinical manifestations of vascular disease or cartilage disease. Most preferably, less than 10% of the human population sample displays clinical manifestations of vascular disease or cartilage disease. It is preferable that the human population sample be minimized with respect to any disease or disorder that would tend to affect levels of serum MGP.

Preferably, serum MGP is detected using an immunoassay. An immunoassay employs the interaction between an antigen (for example, human MGP or a fragment thereof) and an antibody (for example, an antibody or monoclonal antibody, or fragment thereof, directed against human MGP). Serum MGP can be measured using the methods and compositions disclosed herein. Any suitable immunoassay method or platform now known in the art, or that comes to be known, can be used in conjunction with the methods and compositions of the invention. For example, ELISAs, sandwich assays, Western blots, and the like can be used in conjunction with the present invention to detect serum MGP levels.

The methods and compositions of the present invention can be employed in validation of therapies, drugs, protocols or treatments related to (1) vascular calcification, (2) diseases or disorders related to vascular calcification, (3) diseases or disorders of human cartilage, or (3) manipulation of the carboxylation state of MGP, whether directly acting on MGP or acting on a pathway that might result in a change of carboxylation state of MGP. One non-limiting example of such a use is to assay samples from a human over time, using the methods and compositions of the present invention, where the human is a subject in a clinical study of the efficacy or safety of a composition that affects, directly or indirectly, the carboxylation state of human MGP.

The methods and compositions of the present invention can be employed where human MGP and/or one or more of its carboxylated forms, is employed as a surrogate marker for a disease or disorder in a human. The term "surrogate marker" is meant to include the use of a first characteristic of a sample to infer a second characteristic of the sample, or of the organism from which the sample is derived. In this regard, a surrogate marker is typically correlated with a disease or disorder or a susceptibility thereto. For example, the first characteristic can be under-carboxylation or non-carboxylation of human MGP. Or the first characteristic can be, for example, the level of MGP in serum. The second characteristic can be the occurrence of, or susceptibility to, atherosclerosis. The correlation between the first characteristic and the second characteristic need not be perfect. Preferably, the correlation between the first characteristic and the second characteristic is from 0.1 to 0.3 (positive or negative). More preferably, the correlation is from 0.3 to 0.5 (positive or negative). Even more preferably, the correlation is at least 0.5 (positive or negative). Most preferably, the correlation is at least 0.9 (positive or negative).

In order to investigate the potential value of MGP, or a functional part or derivative thereof, as a biomarker for vascular and cartilage characteristics, MGP and fragments thereof were prepared synthetically and assays were developed for the detection both of MGP in tissue, in particular vascular tissue, and of circulating MGP. The methods described herein have been used to construct mAb3-15, mAb35-49[Glu], and mAb35-53[Glu]. The methods described herein can be used to construct other antibodies to human MGP, including, for example, mAb35-49[Gla], mAb35-53[Gla], mAb54-84, and mAb61-79. The methods herein can also be used to develop assays for the detection and assessment of diseases of the cartilage, for example, osteoarthritis, Bechterew's disease, and rheumatoid arthritis.

By way of example, the inventors have determined that in all stages of atherosclerosis, vitamin K-deficiency was demonstrated. See FIG. 14. This identifies atherosclerotic patients as a group who might benefit from vitamin K-supplements, which is of importance for public health and for the health food industry.

MGP, or functional fragments thereof, can be obtained in various ways, for example by recovering from a natural source, chemical synthesis, or using recombinant DNA techniques.

Hybridoma cell line B11 A#1, which produces a monoclonal antibody directed against an epitope in human matrix Gla protein residues 35-49, was deposited on Mar. 23, 2004 with Deutsche Sammlung von Mikroorganismen and Zellkulturen GmbH (DSMZ) located at Mascheroder Weg 1b, D-381124 Braunschweig, Germany as accession number DSM ACC2639. Hybridoma cell line 52.1 #1, which produces a monoclonal antibody directed against an epitope in human matrix Gla protein residues 3-15, was deposited Mar. 23, 2004 with DSMZ, as accession number DSM ACC2638.

In bone, MGP accumulates in relatively large quantities, which is why bone is the only tissue from which native MGP has been isolated thus far (Price, supra). However, under physiological conditions, MGP originating from human and bovine bone is one of the most insoluble proteins known.

The nucleotide and amino acid sequences of human MGP are shown in FIG. 1. Comparison between its primary structure and the amino acid sequence derived from cDNA coding for MGP shows that in bone-derived MGP the last 7 C-terminal amino acids are missing (Hale, J. E. et al., *J. Biol. Chem.*, (1991) 266:21145-21149).

For the purpose of the present invention, synthetic peptides homologous to certain sequences of human MGP, for example, to the MGP sequences 3-15, 35-49[Glu], 35-49 [Gla], 54-84, and 61-79 were synthesized chemically and purified. Sequences as those mentioned above will be referred to hereinafter as $MGP^{3-15}$, $MGP^{35-49}$-[Glu], $MGP^{35-49}$-[Gla], $MGP^{54-84}$, and $MGP^{61-79}$, respectively. Further, polyclonal antibodies were generated using MGP sequences 61-79.

A synthetic peptide homologous to residues 35-53[Glu] and 35-53[Gla] can be synthesized chemically and purified. Such synthetic peptides are designated $MGP^{35-53}$[Glu] and $MGP^{35-53}$[Glu], respectively.

MGP can also be made using recombinant DNA techniques. When produced by recombinant techniques, standard procedures for constructing DNA encoding the antigen, cloning that DNA into expression vectors, transforming host cells such as bacteria, yeast, insect, or mammalian cells, or any suitable expression system known in the art, and expressing such DNA to produce the antigen may be employed. It may be desirable to express the antigen as a fusion protein to enhance expression, facilitate purification, or enhance solubility.

For example, first a DNA encoding the mature protein (used here to include any maturation form) is obtained. mRNA coding for MGP can be isolated from, e.g., cultured human osteoblasts, and converted into the corresponding cDNA using well-known techniques. Alternatively, mRNA coding for MGP can be obtained from other cell types, such as chondrocytes or smooth muscle cells. If the sequence is uninterrupted by introns, genomic or cDNA is suitable for expression in any host. If there are introns, expression is obtainable in eukaryotic systems capable of processing them. This sequence should occur in an excisable and recoverable form. The excised or recovered coding sequence is then placed in operable linkage with suitable control sequences in a replicable expression vector. The vector is used to transform a suitable host and the transformed host is cultured under favorable conditions to effect the production of the recombinant protein. To improve the efficacy of prokaryotic MGP expression, the cDNA may be equipped with an extension encoding a second protein in such a way that expression will give rise to a chimeric fusion protein.

Genomic or cDNA fragments can be obtained and used directly in appropriate hosts, for example, *E. coli*. The constructs for expression vectors operable in a variety of hosts are made using appropriate replication and control sequences, as exemplified below. Suitable restrictions sites can, if not normally available, be added to the ends of the coding sequence so as to provide an excisable gene to insert into these vectors.

The control sequences, expression vectors, and transformation methods are dependent on the type of host cell used to express the gene. Generally, prokaryotic, yeast and other eukaryotic cells (e.g., fungi, mammalian, insect, and plant cells) are presently available as hosts. Host systems which are capable of proper post-translational processing are preferred.

In one embodiment of the present invention, MGP is suitably expressed as a chimeric protein linked to murine dihydrofolate reductase (DHFR) and equipped with a N-terminal 6-His tag for rapid purification; see FIG. 1 and SEQ ID NOS: 1 and 2. The obtained 6-His tagged chimeric protein was poorly soluble under physiological conditions. It is used for coating the microtiter plates in the assay which will be described below. Instead of DHFR, other proteins of sufficient size to efficiently express a chimeric protein with MGP may be selected, known in the art, such as maltose binding protein.

A chemical detection method is used employing one or more monoclonal antibodies. The monoclonal antibody may suitably be human, mouse, rat or *Camelidae* (e.g., llama) monoclonal antibody prepared by conventional methods, including those methods currently available for producing monoclonal antibodies on a commercial scale, genetically engineered monoclonal antibodies, or antibodies fragments or antibodies produced by in vitro immunization by certain cells, and by phage display techniques. Also, one or more polyclonal antibodies can be suitably employed, preferably antibodies generated in rabbit or goat.

The monoclonal antibodies are conveniently generated from mice which are immunized with human MGP or a fragment thereof, for example $MGP^{3-15}$, $MGP^{35-49}$[Glu], $MGP^{35-49}$[Gla]$MGP^{35-53}$[Glu]$MGP^{35-53}$[Gla], $MGP^{54-84}$, or $MGP^{61-79}$. Suitable and preferred monoclonal antibodies against human MGP are obtained from Balb/C mice which are immunized, e.g., with the peptide $MGP^{3-15}$, the peptide $MGP^{35-49}$[Glu], or the peptide $MGP^{35-53}$[Glu], using post-immune sera screening for their affinity toward purified recombinant MGP, which was used as a chimeric construct with DHFR; see below. In parallel, the antisera and culture media were also screened using synthetic peptides as affinity ligands. In this manner, monoclonal antibodies reactive against epitopes in human MGP residues 3-15, 35-49 [Glu], and 35-53[Glu] were created. Monoclonal antibodies directed against other epitopes in MGP, such as those mentioned above and described herein, can be made in accordance with the methods described herein.

Detection and quantitation of circulating MGP, which includes MGP-related antigen, can also be performed in various ways. In accordance with the present invention we have developed an ELISA-based serum assay, a so-called "antibody-capture" assay in which the sample MGP is complexed with an excess of purified monoclonal anti-MGP antibody, whereas in a second step the remaining unbound antibodies are quantified after binding to insolubilized recombinant MGP. Recorded immunoreactive MGP turned out to be independent of sample preparation and showed small within-day and day-to-day fluctuations.

Figure 12:
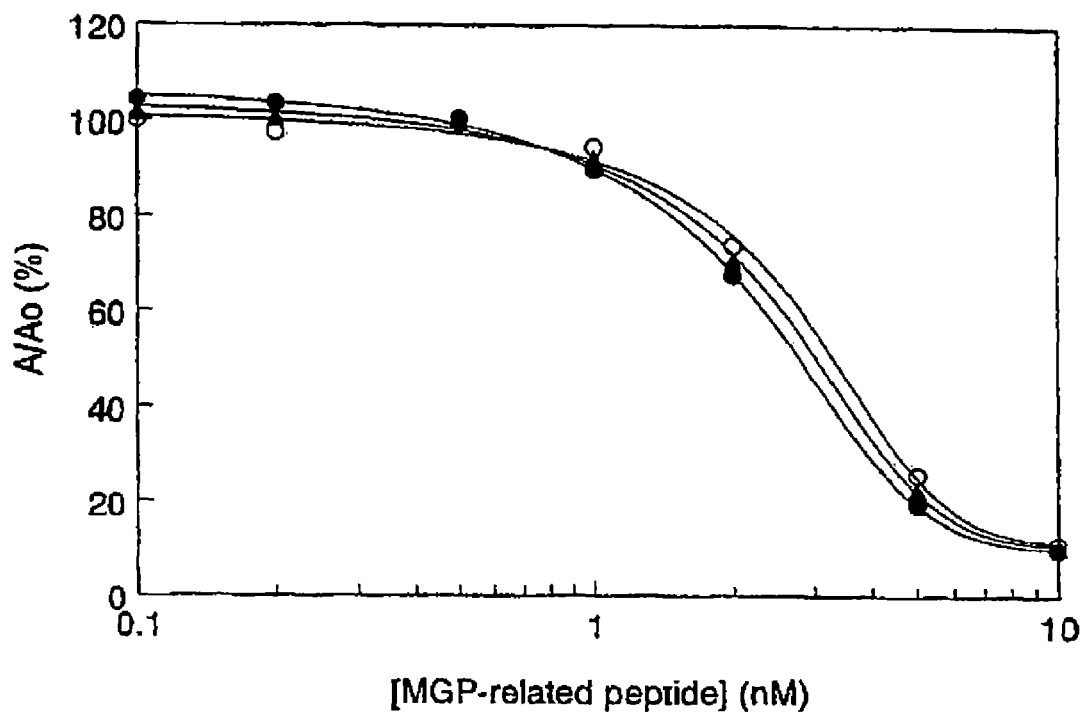
Figure 13:
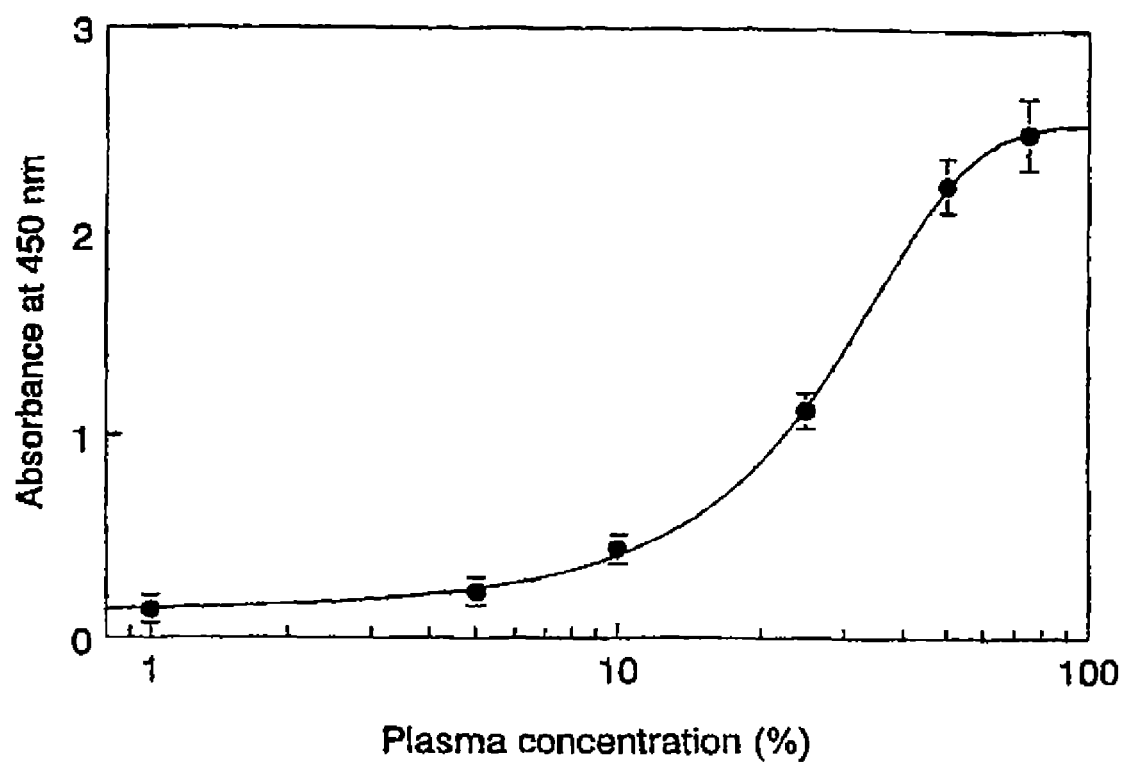
FIG. 13 shows the means of triplicate MGP-measurements in pooled plasma at various plasma dilutions using the sandwich ELISA technique. In this technique monoclonal antibodies against the MGP mid-sequence (mAb35-49) were coated onto the microtiter plate whereas biotinylated mAb3-15 was used as a second antibody. Error bars represent SD.

Besides the antibody capture technique and the competitive ELISA technique, which are both single-antibody ELISA assays, the sandwich ELISA assay can also be conveniently used for the detection and quantification of circulating MGP, depending on the availability of a suitable second antibody. Below we will first describe the development of the antibody-capture technique, followed by a more detailed description of the antigen-capture and sandwich ELISA techniques, respectively, as illustrated in FIGS. 12 and 13.

Dose-response curves were prepared with various dilutions of normal pooled serum and plasma. We found that these curves were reproducible in time with linear curves between 2- and 10-fold dilutions. Intra- and inter-assay variations in control samples were 12 and 15%, and little cross reaction was observed with serum from other species including mouse and cow.

Figure 11:
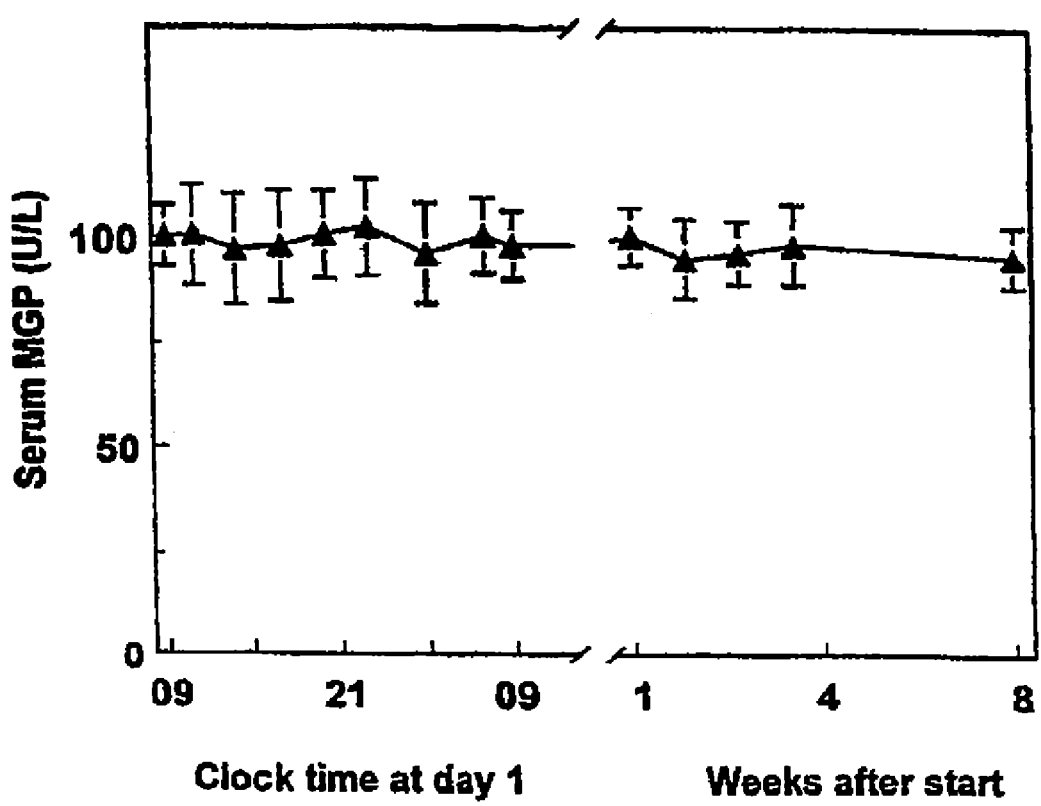
FIG. 11 shows the absence of circadian pattern for circulating human MGP. Points represent means±SD for twelve different subjects; nine blood samples were obtained during the first 24 hours, and 5 samples were obtained at 9 a.m. during the following two months.

No circadian fluctuations were observed in a group of 6 men and 6 women (see FIG. 11). The range in the adult male population was found to be between 60 and 150% of the mean. MGP was independent of age in a reference group of men and women >55 years old. After immunohistochemical staining of vascular material, a low but distinct MGP deposition was observed in medial smooth muscle cells. Strongly increased deposition of MGP was observed in the center of the lipid core in advanced plaques, and in the border zones of mineral deposits.

Since it seems hard to envisage that a focal burst of MGP synthesis would trigger calcification, it seems likely that MGP expression is a response to the precipitating mineral. Diabetics form a high risk group for developing media sclerosis, and therefore we have monitored circulating MGP in this patient group. It turned out that circulating MGP concentrations in type I diabetics (n=12) were significantly higher than in age- and sex-matched healthy controls, and the difference was statistically significant. In a group of 26 patients with coronary atherosclerosis, serum MGP was even further increased. In a cohort of 200 subjects no correlation was found between serum MGP and intima thickness (intima/media ratio). In subjects with postmenopausal osteoporosis or other metabolic bone disease, serum MGP levels were within the normal range.

From the data obtained so far we conclude that our assay for serum MGP is reproducible, that arterial calcification is associated with increased MGP deposition, and that in advanced atherosclerosis the increased MGP synthesis is reflected in its serum concentration. Apart from further elaboration and fine-tuning, which is well within the level of ability of a person of ordinary skill in the art in light of the disclosure of the present invention, the MGP assay is useful as a diagnostic tool for diagnosis or patient follow-up during the treatment of, for example, atherosclerosis and, possibly, related diseases, such as, for example, diseases of cartilage.

The following is a typical example and preferred embodiment of the invention illustrating the preparation of a monoclonal antibody specifically recognizing epitopes and/or conformations on human Matrix Gla-protein, and various other aspects.

EXAMPLES

A. Preparation of Recombinant Human MGP

For cloning and expression of the chimeric construct of murine dihydrofolate reductase and MGP (DHFR-MGP) the commercially available QIAexpress system was used (Qiagen Inc.). Fusion proteins were constructed using the pQE40 vector, which contains an expression cassette consisting of the phage T5 promoter fused to the mouse DHFR protein. To facilitate protein purification by metal chelate affinity chromatography, the recombinant protein was engineered to contain a six residue long histidine tail preceding the DHFR. For in frame fusion with the start codon of the 6-His region the expression vector pQE40 was linearized with the restriction enzymes SphI and HindIII (Gibco BRL). Subsequently, the linearized vector was purified by agarose gel electrophoresis according to standard procedures.

For cloning of the human MGP cDNA, 5'-SphI and 3'-HindIII digestion sites were introduced by the polymerase chain reaction (PCR). Primers MGPHUMT1 and MGPHUMT3 (for details see below) were used for amplification of cDNA coding for Ile-Glu-Gly-Arg-MGP. Each PCR reaction consisted of 5 µl cDNA, 1 mM of each dNTP, 1 µg of each primer, 4 mM $MgCl_2$, 50 mM KCl, 10 mM Tris-HCl pH 8.3, 0.01% gelatin, and 2.5 U of Taq polymerase (Pharmacia) in a total volume of 50 µl. Each PCR cycle consisted of 1 min at 95° C., 2 min at 60° C. and 2 min at 72° C. The amplified cDNA was digested with SphI and HindIII (Gibco-BRL) and the resulting fragments were then separated by agarose gel electrophoresis and isolated thereof by electro-elution. The isolated fragments and linearized vector were then ligated in reactions containing 1 µl digested fragment, 1 µl digested pQE40 vector (in a weight ratio of 3:1), and subsequently transformed into E. coli strain M15[pREP4]. Reaction conditions were: 1× T4 DNA ligase buffer, 1 mM ATP, and 1 Weiss Unit of T4 DNA ligase (Pharmacia Biotech). Ligations were performed overnight at room temperature in a total volume of 10 µl. For the identification of clones expressing a 6-His tagged DHFR protein fused to MGP, the colony blot procedure was used according to the QIA Expressionist manual.

Sequence analyses were performed on an ABI 310 genetic analyzer (Perkin Elmer) according to the cycle sequencing procedure of the manufacturer. In brief, approximately 0.5 µg of $CsCl_2$ purified ds-DNA was added to a reaction mixture which included 8 µl Terminator Ready Reaction Mix (Perkin Elmer) and 5 pmol of an appropriate primer in a total volume of 20 µl adjusted with $H_2O$. Cycle sequencing was performed on a Thermo Cycler 9600 (Perkin Elmer) according to the following protocol. Each cycle consisted of 30 s at 95° C., 15 s at 60° C., and 4 min at 72° C. After 25 cycles, the procedure was terminated by a rapid ramp to 4° C. Subsequently, the products were purified on MicroSpin S-200 HR columns (Pharmacia Biotech) pre-equilibrated in $H_2O$ according to the manufacturer's protocol. Finally, samples were precipitated with ethanol, dried under vacuum, and resuspended in 25 µl of Template Suppression Reagent (Perkin Elmer). Prior to loading the samples on the ABI Prism 310 Genetic Analyser, samples were heated at 95° C. for 2 min. Sequence analysis of the samples was performed according to the manufacturer's manual.

All primers necessary for PCR and cycle sequencing were commercially manufactured by Perkin Elmer or Eurogentec with the following sequences:

```
MGPHUMT1 (5'→3'), for SphI restriction site at
5' end of human Xa-MGP:
                                      (SEQ ID NO: 3)
tat gca tgc att gaa ggt cgt tat gaa tca cat
gaa agc MGPHUMT 3 (5'→3'), for HindIII restriction site
at 3' end of human Xa-MGP:
                                      (SEQ ID NO: 4)
tat aag ctt ttt ggc ccc tcg gcg ctt cct
```

B. Characterization of Expression Product

All DNA fragments obtained through restriction enzyme digestion were purified using the QIAquick PCR Purification Kit (Qiagen).

Ile-Glu-Gly-Arg-MGP cDNA was ligated into pQE40 and resulted in a correct plasmid construct: pQE40-Ile-Glu-Gly-Arg-MGP as was established with $CsCl_2$ purified DNA of the construct, sequenced on an ABI Prism 310 sequencer. It was verified that the construct corresponded to pQE40 Ile-Glu-Gly-Arg-MGP and that it was in the correct reading frame (see FIG. 1; SEQ ID NO:1). Calculated characteristics of the recombinant fusion protein 6His-DHFR-Ile-Glu-Gly-Arg-hMGP are: Mw=34.787 kD, 297 amino acid residues, pI=9.59. The resulting plasmid was transformed into E. coli strain M15 [pREP4].

The construct was transformed into *E. coli* strain BL21 [DE3, pREP4], which is deficient in the lon and ompT proteases. Selection of recombinant protein producing clones through the colony blot procedure and using the 6-His monoclonal antibodies demonstrated several MGP producing clones. From small-scale expression experiments, followed by analysis of the product by poly-acrylamide gel electrophoresis and Western-blotting, cross reaction with 6-His monoclonal antibodies demonstrated a specific binding against a protein with the expected molecular weight of approximately 35 kD and a minor band of 28 kD.

From the foregoing it can be concluded that good expression of the Ile-Glu-Gly-Arg-MGP constructs as a part of a 6-His DHFR fusion protein in the pQE expression vector was accomplished in *E. coli* strain BL21 [DE3, pREP4].

C. Preparation of Monoclonal Antibodies

Balb/C mice were immunized intraperitoneally either with a synthetic peptide homologous to the N-terminus of human MGP (residues 3-15), or synthetic peptides homologous to the mid-fragment of human MGP (residues 35-49[Glu]); or a synthetic peptide homologous to the C-terminus of human MGP (residues 54-84), which were coupled respectively to keyhole limpet hemacin (KLH from Pierce, product nr. 77107). The antigen (20 µg) was mixed with Freund's complete adjuvant and used for the first immunization. The animals were boostered every second week with 20 µg of antigen in Freund's incomplete adjuvant. Post-immune sera were screened with an indirect ELISA using purified recombinant 6-His-DHFR-Ile-Glu-Gly-Arg-hMGP derived from *E. coli*, as described below.

For the screening of post immune sera of mice and cell supernatants an indirect ELISA was used in which the purified recombinant protein 6-His-DHFR-Ile-Glu-Gly-Arg-hMGP was bound to the solid phase. The stock solution of protein was diluted with sodium carbonate buffer (0.067 M $NaHCO_3$, 0.033 M $Na_2CO_3$, pH 9.6) to the required concentration (e.g., 50 fold), and used to coat the wells of a 96-well microtiter plate (Costar, cat. no. 3590) by incubation for 1 hour at 37° C. After coating, the plates were washed three times with washing buffer (0.3% Tween-20 in phosphate buffered saline) and 50 µl of either post-immune serum or cell supernatant were transferred into the coated microtiter plates and incubated for one h at 37° C. to achieve complete binding of the antibodies. Plates were washed three times with washing buffer and subsequently incubated for one h at 37° C. with 50 µl of a solution containing 1 µg/ml of rabbit anti mouse immunoglobulin conjugated to horseradish peroxidase (Dako, product nr. P0161) in washing buffer. Non-bound conjugated antibodies were removed by washing and 50 µl of TMB substrate (Roche) were transferred to each well; after 10 minutes reaction was stopped with 100 µl of $H_2SO_4$. Optical densities were read at 450 nm in an EIA reader (Bio-Rad, model 550). Post immune sera were diluted 100 times in 2% non fat dry milk (Protifar from Nutricia Holland) in phosphate buffered saline before use.

Spleen cells of good responding mice were fused with Sp 2/0 Ag 14 myeloma cells. Cell suspensions were dispensed in ten 96-well microtiter plates and hybridomas were cultured for first 5 days in HAT selective medium containing RPMI 1640 medium (Gibco, cat. nr. 21060-017), 15% fetal clone serum (Hyclone-Greiner, cat nr. A-6165), 1 mM pyruvate (Gibco, cat. nr. 11840-048), 2 mM L-glutamin (Serve, product nr. 22942), growth factor ESG (Costar), 1 mg/ml gentamycin (A.U.V. Cuijk Holland, cat. nr. VPK 62389) and 2% (v/v) 50× HAT. After 5 days half of the medium was refreshed with medium with same contents except that HAT was replaced by 2% (v/v) 50× HT (Gibco, cat. nr. 41065-012). After 11 days the cell supernatants of hybridoma cells were screened using the ELISA technique described above. Single cell cloning of positive hybridoma cultures was performed by limiting dilution (see: *Antibodies, A Laboratory Manual* by E. Harlow and D. Lane, 1986, p. 222). This technique was repeated two more times for obtaining a monoclonal hybridoma cell line.

The antibody producing hybridoma clone was grown in a roller bottle flask with 1 liter RPMI 1640 medium containing 3% fetal clone serum, 1 mM pyruvate, 2 mM L-glutamin and gentamycin at 37° C. for two weeks. Culture media were separated from the cells by centrifugation, and IgG was isolated from the cell supernatants by protein-G Sepharose column chromatography (Pharmacia, cat. nr. 17-0618-02). Eluate fractions with $A_{280}$>0.1 were pooled and concentrated using a concentrator filter with a 10 kD cut-off value. The yield was approximately 20 mg IgG per liter of culture medium, the material obtained was stored at −20° C. at a concentration of 1 mg/ml.

In a similar way antibodies against other peptides, $MGP^{39-49}$[Glu], and $MGP^{35-53}$ [Glu], have been prepared.

Similarly, antibodies against other peptides, such as $MGP^{35-49}$[Gla], $MGP^{35-53}$[Gla], $MGP^{61-79}$, and $MGP^{54-84}$ can be prepared.

D. Characterization of Antibodies

Antibodies were characterized by the Western blot technique, in which total bacteria lysates were separated using an SDS-page minigel electrophoresis apparatus (Bio-Rad). After electrophoresis had been completed, the proteins were transferred to a nitrocellulose membrane by blotting. Staining with the antibody resulted in a distinct protein band at 35 kDa. This is the expected molecular weight of the fusion protein 6-His-DHFR-Ile-Glu-Gly-Arg-hMGP. Monoclonal antibodies are of subclass type $IgG_1$ as determined with the mouse monoclonal antibody isotyping kit (Gibco, cat no. 10126-027). The monoclonal antibodies thus prepared will also be referred to as mAb3-15, mAb35-49[Glu], and mAb35-53 [Glu], respectively. Preferred monoclonal antibodies of the present invention are mAb3-15 and mAb35-49[Glu]. Monoclonal antibodies can also be prepared against human MGP residues, such as, for example, $MGP^{35-49}$[Gla], $MGP^{35-53}$[Gla], $MGP^{54-84}$, and $MGP^{61-79}$ which would be designated mAb35-49[Gla], mAb35-53[Gla], mAb54-84, and mAb61-79, respectively. Preferred monoclonal antibodies of the present invention would include mAb35-49[Gla] and mAb35-53[Gla].

E. The Use of Antibodies in Assays for Circulating MGP

Three procedures for the MGP assay were worked out: the antibody-capture ELISA and the competitive ELISA both enable the detection of full length and fragmented MGP, and the sandwich ELISA, which allows the specific recognition of intact molecules only.

E1. Procedure for the Antibody-Capture ELISA

In this assay a known excess of antibody is mixed with the test solution containing an unknown amount of antigen, and the mixture is added to a microtiter plate coated with antigen.

Non-bound antibody from the test sample will be bound to the microtiter well, and is quantified with a second (labeled) antibody.

- Urea-solubilized recombinant 6His-DHFR-Ile-Glu-Gly-Arg-hMGP is diluted 50 fold with coating buffer (0.1 M sodium carbonate buffer, pH 9.6) and used for coating an excess of 6His-DHFR-Ile-Glu-Gly-Arg-hMGP of the microtiter plates (50 µl in each well), the plates are allowed to stand for 1 h at 37° C.;
- Remaining active sites are blocked with blocking buffer (Roche Diagnostics Blocking reagent, cat nr. 1 112 589), 100 µl/well for 1 h at 37° C.;
- After repeated washing with washing buffer (0.3% (w/v) Tween-20 in phosphate-buffered saline) the plates are ready for use;
- Serum or plasma samples are supplemented with antibody solution (1 µg/ml in 3% (w/v) bovine serum albumin in phosphate-buffered saline) and incubated for 5 min at room temperature;
- The samples (50 µl) are than transferred to the microtiter plates and incubated for 1 h at 37° C.;
- After washing 3 times with PBS/Tween buffer (see above) the amount of antibody bound to the plate is quantified using a second antibody: rabbit anti-mouse total IgG labeled with horse radish peroxidase (Dako, 1 µg/ml in PBS-Tween buffer) for TMB-staining (TMB enzymatic kit from Roche);
- After 15 min incubation the reaction is stopped by adding 1 M $H_2SO_4$ whereafter the plate is read at 450 nm.

E2. Procedure for the Competitive ELISA

In this assay a known amount of labeled antigen (the tracer) is mixed with the test solution containing an unknown amount of antigen, and the mixture is added to the microtiter-bound antibody. The antigen in the test solution will compete with the tracer for binding to the antibody matrix.

- Biotinylation of tracer. A synthetic peptide analogous to the amino acid sequence 3-15 in human MGP ($MGP^{3-15}$) is used as a tracer. Biotin-X-NHS (Calbiochem # 2031188) is diluted in dimethyl sulfoxide (DMSO) to a final concentration of 10 mg/ml and added to $MGP^{3-15}$ (2 mg/ml in 0.1 M Na-borate buffer pH 8.5). Incubate at room temperature for 3 h in the dark. Remove the unbound biotin by overnight dialysis against phosphate buffered saline (PBS) and store the labeled peptide in the dark at 4° C. after adding sodium azide to a final concentration of 0.1% (w/v).
- Coating of microtiter plates. mAb3-15 antibodies (5 mcg/ml in carbonate buffer, pH 9.6, 0.1 ml per well) are immobilized in wells of a high binding 96-well microtiter plate (Corning # 3590). After incubation for 1 h at 37° C. remaining active sites are blocked with blocking reagent (Roche, 0.125 ml for 1 h at room temperature). All subsequent washing steps between the various incubations are performed with 0.05% (v/v) tween-20 in 0.225 ml PBS.
- Sample preparation. Prepare the following sample tubes:
    - non-specific signal tube (blanc): 0.250 ml PBS/Tween (0.05%, v/v)
    - total signal tube: 0.125 ml PBS-Tween (0.05% v/v)
    - unknown sample tube: 0.120 ml PBS-Tween (0.05%, v/v)+0.05 ml sample
    - standard tubes containing 0.125 ml of unlabelled $MGP^{3-15}$ in concentrations: 20, 10, 4, 2, 1, 0.4, and 0.2 nM.
- Add 0.125 ml of tracer (0.2 nM in PBS/Tween (0.05%, v/v) to all tubes except the non-specific signal tube and vortex. Transfer 0.1 ml of each tube into a well of the abovementioned microtiter plate and incubate for 1 h at 37° C.
- Measurement. After washing, 0.1 ml of avidin-labeled horse radish peroxidase (0.1 mcg/ml) in PBS containing 10 mg/ml of bovine serum albumin) is added. Incubate for 30 min at 37° C. After two additional washing steps with PBS (to remove all Tween detergent), 0.1 ml of freshly prepared TMB substrate (TMB substrate kit, Pierce) is added to each well. After 15 min incubation at room temperature the reaction is stopped by adding 0.1 ml of 2 N $H_2SO_4$, and the optical density is measured at 450 nm using an ELISA plate reader.
- Calculation.
    - Subtract $OD_{450}$ of the non-specific signal tube from all others
    - Divide corrected $OD_{450}$ of standards and unknowns by OD of total signal: $A/A_0(\%)=OD$ of unknown or standard$\times 100\%$/OD of total signal
    - Make logistic curve fit with standards and interpolate MGP values of unknown samples.

E3. Procedure for the Sandwich ELISA (1)

In this assay two antibodies directed to different epitopes of one antigen are used. One antibody is purified and bound to the solid phase of a 96-well microtiter plate and the antigen in a test solution is allowed to bind. Unbound proteins are removed by washing, and the labeled second antibody is allowed to bind to the antigen. After washing, the assay is quantified by measuring the amount of labeled second antibody that is bound to the matrix. The procedure described here is for antibodies mAB35-49 and mAb3-15, but is applicable for other antibodies as well.

- Coating of microtiter plates. mAb35-49 antibodies (5 mcg/ml in carbonate buffer, pH 9.6, 0.1 ml per well) are immobilized in wells of a high binding 96-well microtiter plate (Corning # 3590). After incubation for 1 h at 37° C. remaining active sites are blocked with blocking reagent (Roche, 0.125 ml for 1 h at room temperature). All subsequent washing steps between the various incubations are performed with 0.05% (v/v) Tween-20 in 0.225 ml PBS.
- Sample preparation.
    - 0.075 ml of unknown plasma are supplemented with 0.225 ml of wash buffer
    - reference samples are prepared by diluting pooled plasma with wash buffer in concentrations of: 75%, 50%, 25%, 10%, 5%, 1%, 0.5% and 0.1%.
    - non-specific signal tube: 0.3 ml of wash buffer
    - transfer 0.1 ml of each sample to microtiter plate wells, incubate 1 h at 37° C.
- Measurement. After washing, 0.1 ml of second antibody solution (5 mcg/ml biotinylated mAb3-15) is added to each well and incubated for 1 h at 37° C. After washing 0.1 ml of Vectastain™ ABC reagent (Vector laboratories) is added to each well and incubated for 30 min at 37° C. After two additional washing steps with PBS to remove all Tween detergent, 0.1 ml of freshly prepared TMB substrate (TMB substrate kit, Pierce) is added to each well. After 15 min incubation at room temperature the reaction is stopped by adding 0.1 ml of 2 N $H_2SO_4$, and the optical density is measured at 450 nm using an ELISA plate reader.
- Calculation.
    - Subtract the average $OD_{450}$ of the non-specific signal tube from all others Make logistic curve fit with standards and interpolate MGP values of unknown samples.

E4. Procedure for the Sandwich ELISA (2)

For the principle of this test, see the introduction under E3, above.

Mouse anti-MGP$^{3-15}$ (1 µg/ml in 0.1 M Na-carbonate buffer, pH 9.6) was coupled to the microtiter plate by pipetting 50 µl of this solution per well, and incubating the plates for 1 h at 37° C.;

Remaining active sites are blocked with blocking buffer (Roche Diagnostics Blocking reagent, cat nr. 1 112 589) 100 µl/well for 1 h at 37° C.;

After repeated washing with washing buffer (0.3% (w/v) Tween-20 in phosphate-buffered saline) the plates are ready for use: either serum or purified MGP are pipetted in the well (50 µl), incubation for 60 min at 37° C.;

Non-bound material is removed by washing with PBS-Tween buffer;

The second antibody (mouse anti-MGP$^{54-84}$, conjugated with horse-radish peroxidase) is pipetted (50 µl, 1 µg/ml), and the plates are incubated for 60 min at 37° C.;

After washing 3 times with PBS/Tween buffer the amount of antibody bound to the plate is quantified using TMB-staining (TMB enzymatic kit from Roche);

After 10 min incubation the reaction is stopped by adding 1 M H$_2$SO$_4$ whereafter the plate is read at 450 nm.

F. Calibration Curve and Test Characteristics

An example of serum and plasma dilution curves obtained with the antibody capture ELISA is shown in FIG. 2. Calibration curves were made on 12 different days using six different dilutions of pooled reference serum. Each dilution was measured in duplicate, and the mean optical densities (OD) at 450 nm (SD) were expressed as a function of the serum concentration (FIG. 2). At increasing dilutions of the serum sample, more anti-MGP was bound to the plate, with the buffer value as a theoretical maximum. The lower detection limit was defined as the mean OD+three times the standard deviation of the buffer value, and amounted 2.096–3× 0.089=1.829, corresponding with an MGP concentration of 8.5 U/L. The intra- and inter-assay variation of the test were determined using a four-fold dilution of the reference serum. The intra-assay variation was calculated by expressing the standard deviation as a percentage of the mean obtained from 21 replicates, repeated on three different days and amounted 5.4%. For assessment of the inter-assay variation, duplicate measurements were made on 14 consecutive days after which the standard deviation was expressed as a percentage of the means to give a value of 12.6%.

In later experiments a gradual improvement can be seen, i.e., the buffer values (no serum added) are somewhat higher, and the plateau values at high MGP concentrations are lower. This depends on factors such as staining time, etc.

The procedure for the antibody capture assay and for the competitive ELISA are similar for each of the monoclonal antibodies. A sandwich ELISA for full length MGP can be made by using one antibody against the N-terminus of MGP (mAb3-15) in combination with one antibody against the C-terminus (mAb61-79). A sandwich ELISA specifically detecting undercarboxylated species of MGP is constructed by using one antibody raised against a peptide outside the Gla-domain (for example, either mAb3-15, which has been produced by the inventor, or mAb61-79, which can be produced in accordance with the procedures described herein) in combination with one conformation-specific antibody (either mAb35-49[Glu] or mAb35-53[Glu]. A sandwich ELISA specifically detecting carboxylated species of MGP can be constructed by using one antibody raised against a peptide outside the Gla-domain (for example, either mAb3-15 or mAb61-79) in combination with one conformation-specific antibody (for example, either mAb35-49[Gla] or mAb35-53 [Gla]).

G. Validity of the Competitive ELISA Using Anti-MGP3-15

Figure 3:
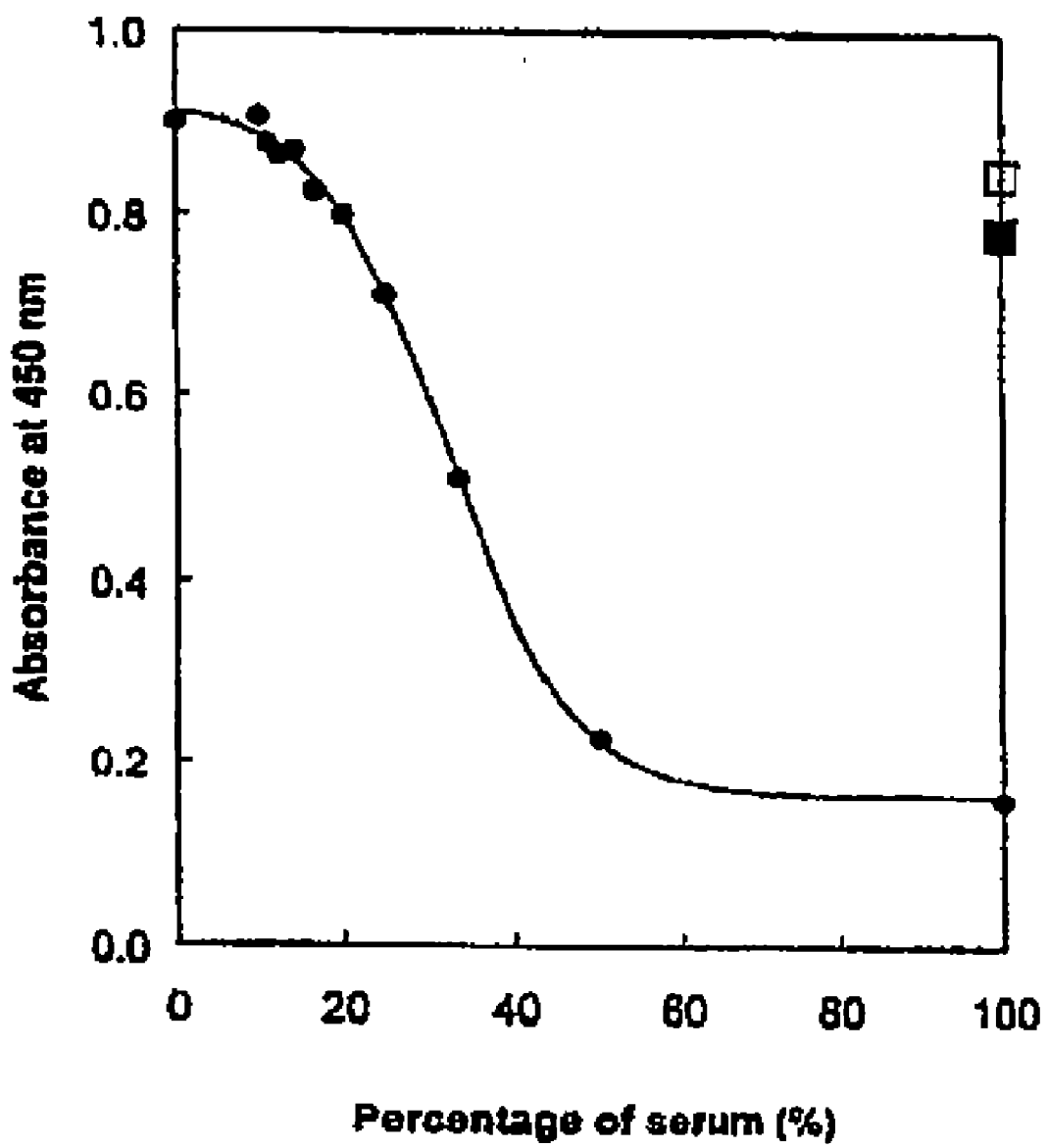
FIG. 3 shows the species specificity of MGP-assay. A dose-response curve for human serum MGP was compared with undiluted rat (□) and mouse (~) serum. No response was obtained for the rodent sera.

Evidence for the validity of the test was obtained from its species specificity: whereas a good response was obtained with human serum, rat and mouse serum gave a poor response (FIG. 3). This must be due to the 2 amino acid residue difference between the rodent and human MGP sequence 3-15.

Figure 4:
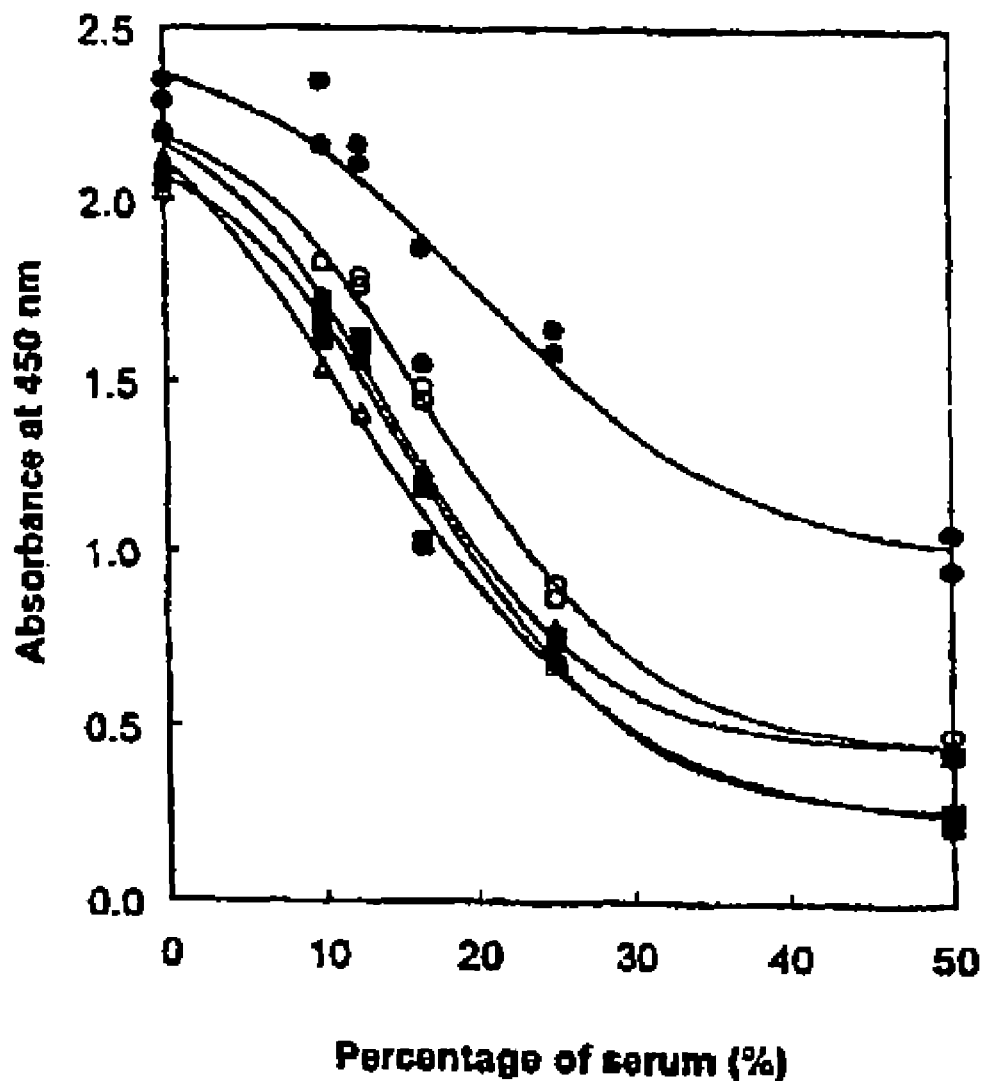
FIG. 4 shows inter-individual variations in serum MGP levels. Five volunteers (30-50 year old males) were tested.

Samples from five different volunteers were tested in duplicate, showing a good reproducibility and curves four of which were in the same range, whereas there was one outrider (FIG. 4).

For assessment of the normal range and reference groups, apparently healthy subjects were recruited among the Maastricht population. The 'normal range' for MGP was established in 80 apparently healthy men between 20 and 84 years of age. It was found that the mean value for serum MGP in this group was 96±17 U/L. Hence the normal range (defined as the mean±2 SD) was calculated to be between 62 and 130 U/L. No apparent age-dependence was observed for MGP in this group. Similar data were observed for elderly women (>60 years of age), but a larger range was found in women between 20-55 years. This may be related to hormonal changes, and forms the basis for our decision that women <60 years old were not included in the experiments presented here.

The day-to-day and within-day variations were determined in a group of 12 healthy men (20-35 years old), from whom blood was taken by venipuncture on nine time points of one day, and on 4 different days at 09.00 a.m. with one week intervals. The day-to-day and within-day variations were determined in a group of 12 healthy men (20-35 years old), from whom blood was taken by venipuncture on nine time points of one day, and on 4 different days at 09.00 a.m. with one week intervals. The within-day variation was calculated for each subject separately by expressing the standard deviation as a percentage of the mean of the nine time points, and amounted 11%. No distinct circadian pattern was observed. The day-to-day variation was calculated in a similar way from the four samples obtained with weekly intervals, and was found to be 8%.

Figure 5:
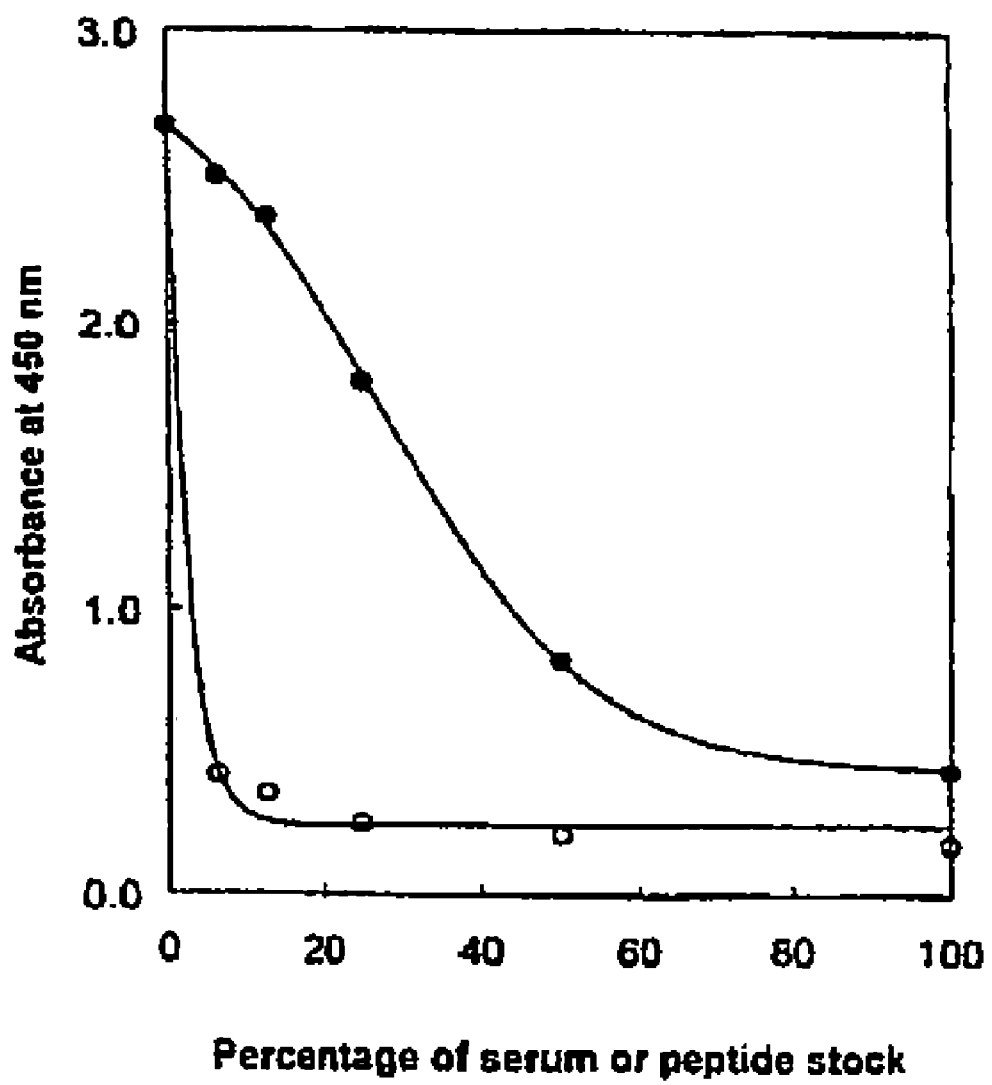
FIG. 5 shows blocking MGP antibodies with peptide 3-15. The stock solution (100%) of peptides was 1.3 µg/ml. Peptide dilutions (□) instead of serum were incubated with antibodies and the excess of antibodies was assessed with the microtiter plate assay. For comparison, reference serum in various dilutions (□) was taken in the same run.

The antibodies were tested further by incubating them with highly diluted peptide MGP3-15. Even at concentrations as low as 0.09 µg/ml the buffer value was almost completely blocked (FIG. 5).

Each of the procedures described above can be used for validation of assays using different antibodies against human MGP.

H. Sample Preparation

To further evaluate the robustness of the assay, we have checked the influence of variations in the sample preparation at the following steps: centrifugation speed (1,500 and 10,000×g) during serum preparation, centrifugation (10,000× g) after adding of mAb$^{3-15}$, freeze-thawing of the serum sample (up to 8 cycles of freeze-thawing) and incubation time (between 3 and 60 minutes at room temperature) of the serum sample with mAb$^{3-15}$. In none of these cases did the sample treatment measurably affect the observed MGP concentration.

Each of the procedures described above can be used for validation of assays using different antibodies against human MGP.

I. Assay Specificity

Figure 10:
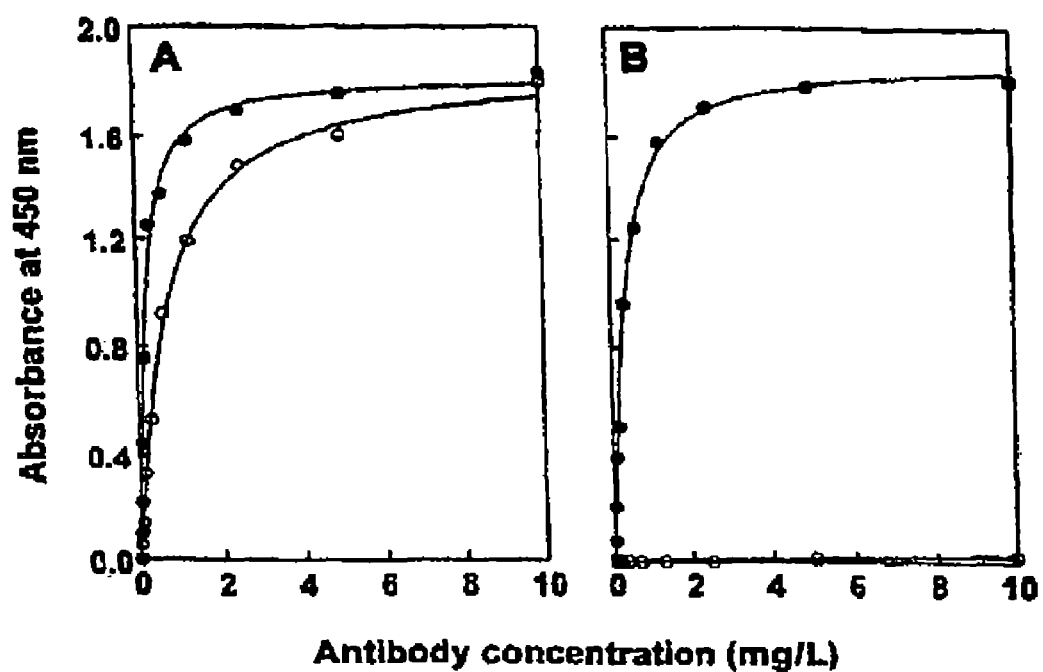
FIG. 10 depicts the reactivity of $mAb^{3-15}$ antibodies with purified rMGP (A) and rOC (B). The amount of recombinant protein on the microtiter plate was quantitated with anti-6His antibodies (□), the reactivity with $mAb^{3-15}$ was tested in the same plate (□). In both cases staining was performed by incubation with a second antibody (rabbit anti-mouse total IgG conjugated with horseradish peroxidase) as described below in Materials and Methods.

The mAb$^{3-15}$ used in the assay was tested for its ability to differentiate between two recombinant bone Gla-proteins: osteocalcin and MGP (both as chimeric constructs linked with 6His-DHFR). Microtiter plates were coated with either purified recombinant MGP (1 μg/well) or equimolar amounts of purified recombinant osteocalcin. Coupling efficiency of both proteins was checked with anti-6-His antibodies. As is shown in FIG. 10, both plates contained similar amounts of recombinant protein (A: MGP; B: osteocalcin), and mAb$^{3-15}$ reacted well with MGP, but not with osteocalcin. The species specificity of mAb$^{3-15}$ was tested further by comparing their reaction with human, rat, and murine serum. Cross reaction with rodent sera was below the detection limit (<8.5 U/L) in all dilutions tested.

Each of the procedures described above can be used for validation of assays using different antibodies against human MGP.

J. Application and Potential Diagnostic Value of the MGP-Assay

J1. Cardiovascular

Figure 6:
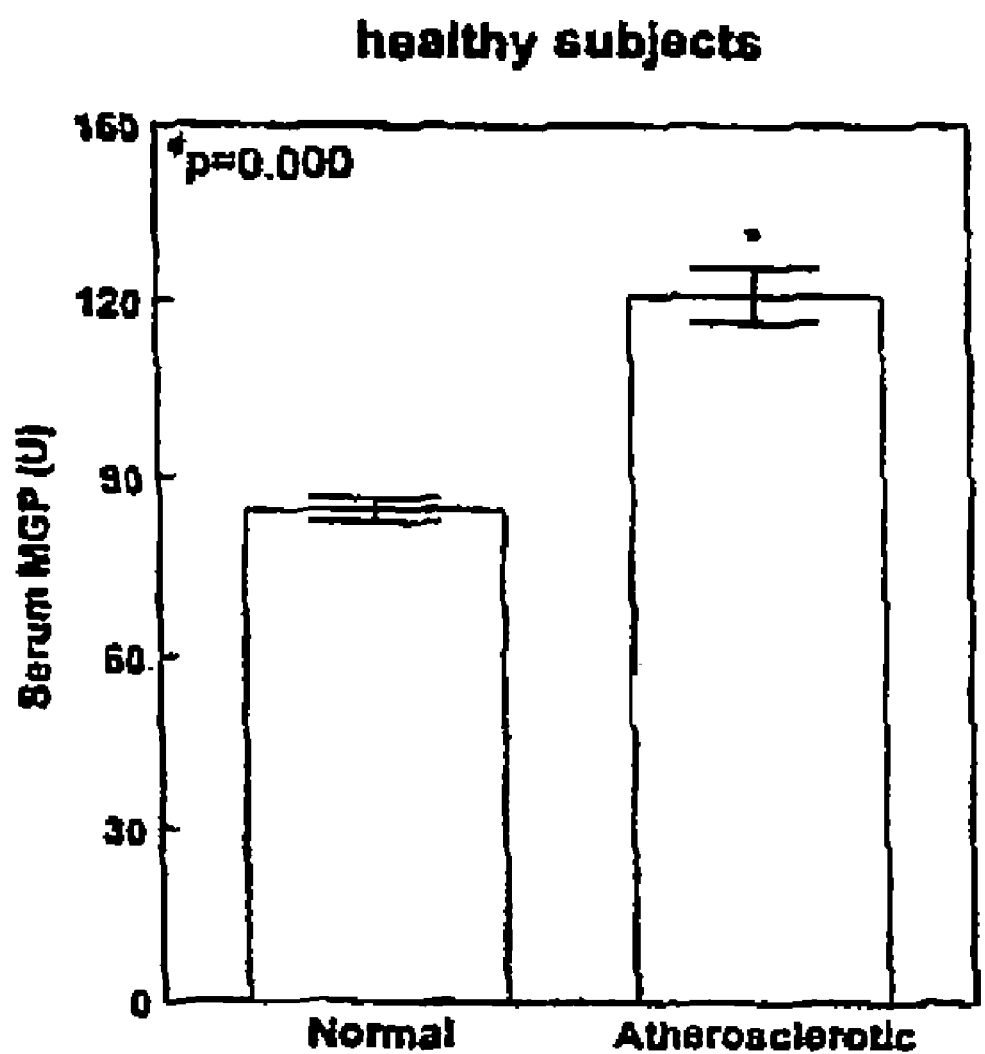
FIGS. 6-9 show serum MGP concentrations of patients suffering from atherosclerosis, coronary atherosclerosis, diabetes mellitus and malignancies, respectively, and of comparative groups of healthy people. These results are also summarized in Table 1.

In a group of over 500 non-hospitalized men between 40 and 60 years old the calcification of the abdominal aorta was measured by X-ray, and 28 subjects with severe calcifications were selected. Circulating MGP was significantly higher in those with calcifications than in those in an apparently healthy age- and sex-matched reference population ($p<0.0001$, see FIG. 6).

J2. Coronary Atherosclerosis

Figure 7:
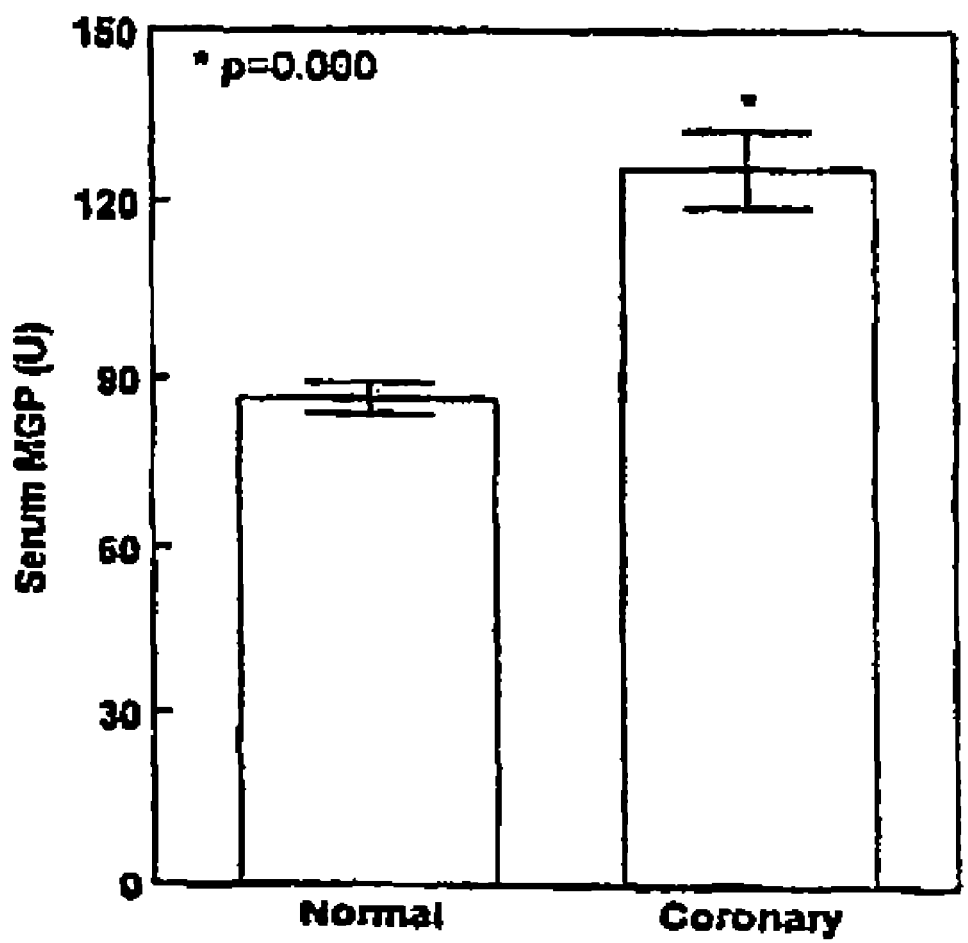

Patients with coronary atherosclerosis (n=26) were recruited from the University Hospital, and their serum MGP was compared with that of the reference population. Serum MGP was significantly increased in the patient group ($p<0.001$, see FIG. 7).

J3. Diabetes Mellitus

Figure 8:
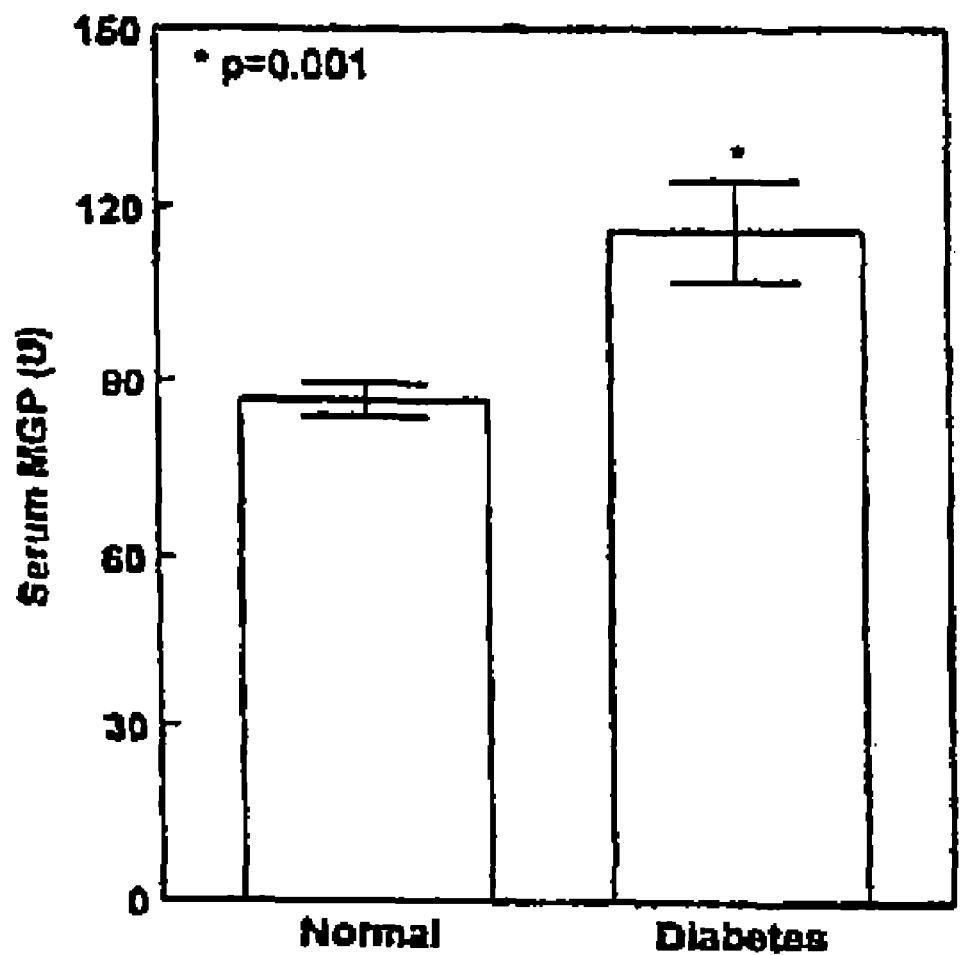

Patients with type I diabetes mellitus (n=23) were recruited from the University Hospital, and their serum MGP was compared with that of the reference population. Diabetes mellitus is a strong risk factor for atherosclerosis. Serum MGP was significantly increased in the patient group ($p<0.01$, see FIG. 8). Patients were selected independent on the duration of the disease.

J4. Malignancies

Figure 9:
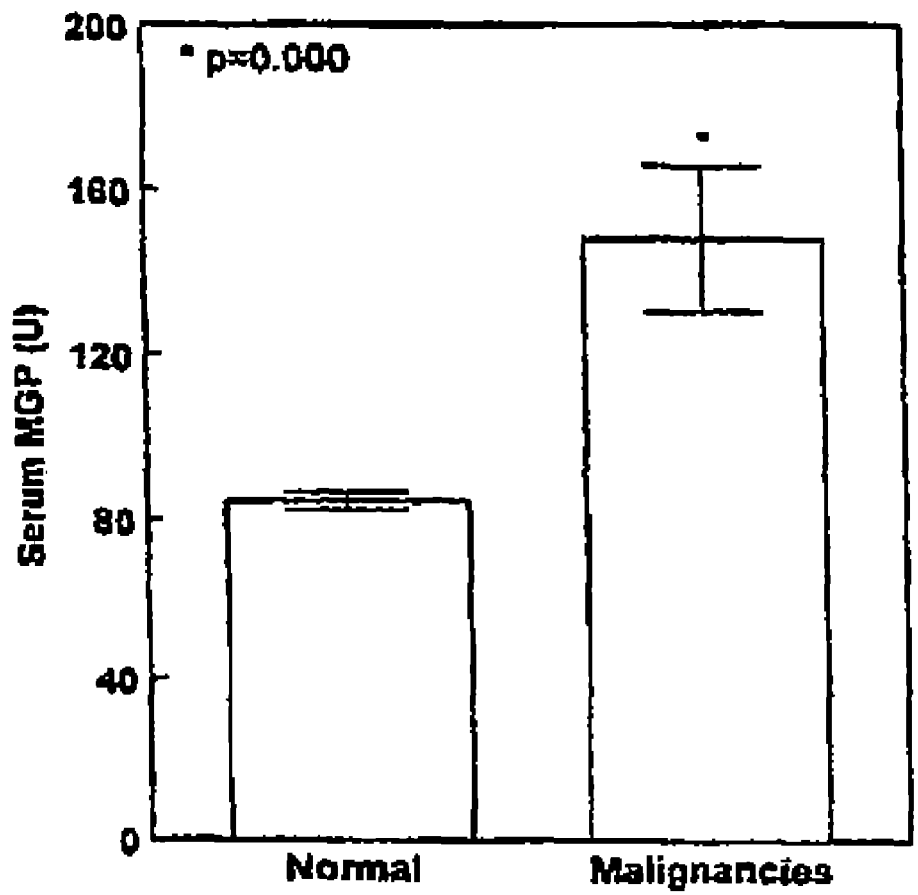

Patients with various malignancies (n=15) were recruited from the University Hospital, and their serum MGP was compared with that of the reference population. Serum MGP was substantially and significantly increased in the patient group ($p<0.0001$, see FIG. 9). Malignancies will often lead to angiogenesis (new formation of blood vessels).

J5. Other Diseases

No correlations were found with early signs of atherosclerosis (increased intima-media thickness) nor with various diseases not related to the cardiovascular system (see Table 1). This suggests that the newly developed assay is specific for diseases of the cardiovascular system, but many other patient groups have to be evaluated in this respect.

TABLE 1

SERUM MGP CONCENTRATIONS IN PATIENTS

| Condition | Number | Serum MGP (% of age- and sex-matched controls) |
|---|---|---|
| High femur BMD (mean + >1SD) | 40 | 98.5 ± 5.7 |
| Low femur BMD (mean − <1SD) | 38 | 102.0 ± 5.2 |
| Senile osteoporosis | 28 | 101.8 ± 6.8 |
| Increased intima/media thickness | 43 | 97.3 ± 6.1 |

Data are given ±SE. Increased intima/media thickness was the highest quartile from a group of 200 apparently healthy elderly subjects. Subjects with high and low BMD of the femur neck were obtained from a reference population (n=250) recruited among the Maastricht population. Patients with osteoporosis, diabetes mellitus and atherosclerosis were obtained via various departments of the University Hospital Maastricht. MGP was measured using human MGP mAb$^{3-15}$.

J6. Serum MGP in Health and Disease

In an analysis of cardiovascular patients, we found that two groups (diabetics and non-diabetics) presenting with angina pectoris and selected for percutaneous angioplasty were characterized by remarkably low serum MGP concentrations. Surprisingly, normal MGP levels were observed in most subjects shortly after cerebrovascular accident and myocardial infarction. In patients with diseases of the cartilage, such as osteoarthritis and Bechterew's disease, the circulating MGP concentrations were also significantly below normal. Except in the Bechterew population, the mean age of all patient groups was slightly higher than that of the reference population; after adjustment for age the differences remained significant in all cases. Normal MGP values were observed in a number of other conditions including postmenopausal osteoporosis (T-score <−2.5). Very high MGP levels were found in renal dysfunction. This may be due to impaired renal filtration, because in these patients also other serum markers such as creatinin and osteocalcin were substantially increased (data not shown).

We observed that serum MGP was significantly decreased in subjects with angina pectoris, where angina pectoris patients exhibit circulating MGP levels that are 50% that of the normal population. In the group of diabetics all subjects presenting with chest pain were included in the study, whereas the non-diabetics consisted of subjects who underwent percutaneous angioplasty 6 months before blood sampling. These data are consistent with a recent publication in which an inverse correlation was observed between the extent of calcification in coronary artery disease and serum MGP concentrations. Remarkably, samples taken shortly after an acute cardiovascular event (myocardial infarction and cerebrovascular accident) were in the normal range. This apparently confusing result may be brought about by two opposite effects: subjects with low constitutive levels of MGP expression are at risk for developing arterial calcifications, but in and around the atherosclerotic lesions MGP expression is stimulated substantially. At certain disease states the locally induced MGP production may compensate for the low synthesis in healthy tissue, resulting in apparently normal circulating MGP levels. So it seems that serum MGP can serve as a marker for cardiovascular risk assessment.

It is also clear that in diseases associated with cartilage destruction and calcification such as osteoarthritis and Bechterew's disease, serum MGP is low as well. The very high MGP levels found in patients with end-stage renal disease were probably the result of poor filtration rather than of high protein expression.

TABLE 2

Serum MGP in health and disease.

| Patients: | number | MGP (nM) | p |
|---|---|---|---|
| Reference population | 121 | 11.2 ± 3.5 | — |
| Cardiovascular diseases: | | | |
| angina pectoris in diabetics | 28 | 5.1 ± 1.2 | <0.001 |
| angina pectoris in non-diabetics | 151 | 6.2 ± 1.9 | <0.001 |
| myocardial infarction | 16 | 11.5 ± 4.6 | 0.82 |
| cerebrovascular accident | 47 | 10.9 ± 4.1 | 0.32 |
| Diseases of the cartilage: | | | |
| osteoarthritis | 28 | 9.0 ± 2.8 | 0.004 |
| chondropathy | 37 | 8.7 ± 2.3 | <0.001 |
| Bechterew's disease | 48 | 8.8 ± 2.4 | <0.001 |
| Other diseases: | | | |
| postmenopausal osteoporosis: | 72 | 11.0 ± 4.6 | 0.79 |
| end-stage renal dysfunction | 14 | 18.2 ± 6.9 | 0.013 |

Legend:
Reference samples were from an apparently healthy adult population.
Patient samples were obtained from cohorts selected for various studies. In all cases the patients had agreed in using their serum for assessment of new biomarkers. All values are expressed as means ± SD.
The values (as a percentage of the reference population) are:
angina pectoris in diabetics: 45.5% ± 10.7
angina pectoris in non-diabetics: 55.3% ± 16.9
osteoarthritis: 80.3% ± 25
Bechterew's disease: 78.5% ± 21.4
chondropathy: 77.6% ± 20.5

Figure 14:
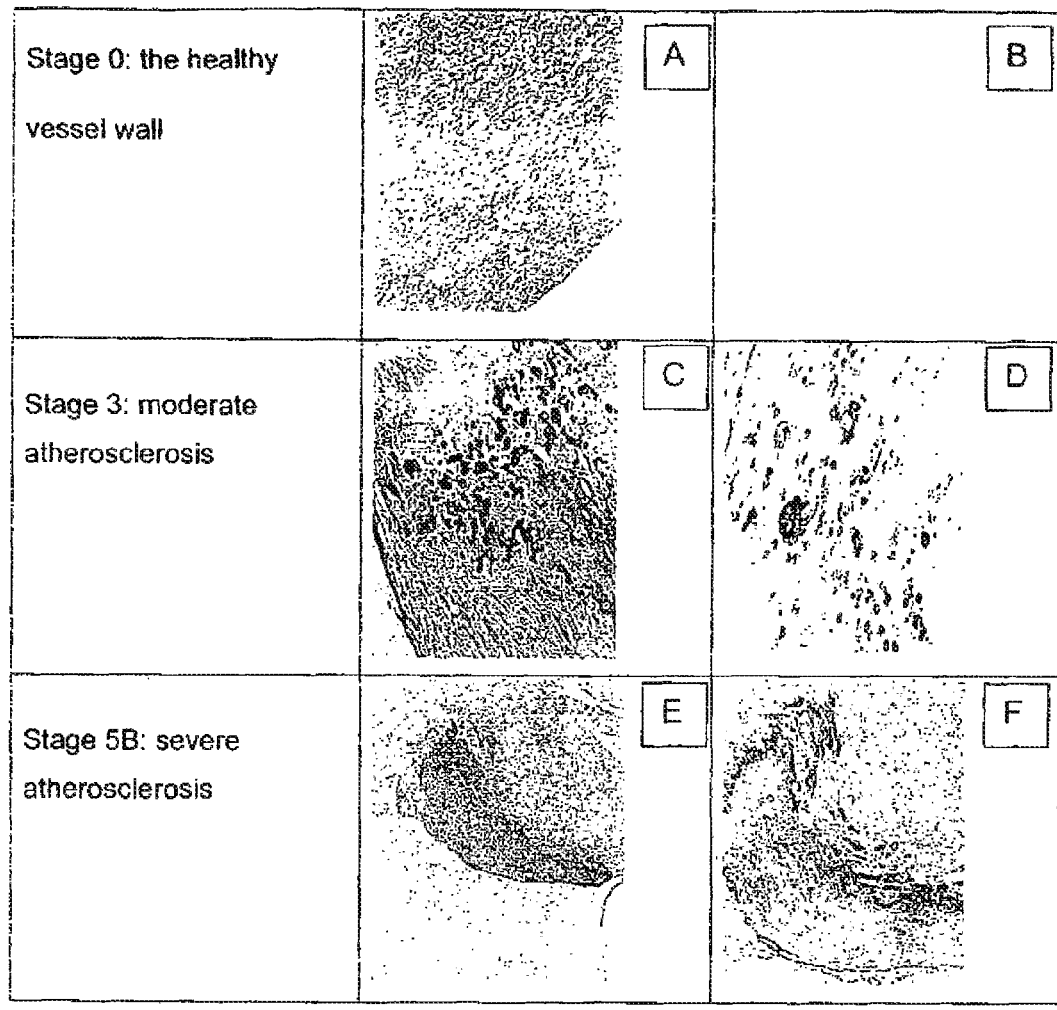
FIG. 14 illustrates immunohistochemical localization (pink color) of MGP species in coronary atherosclerosis. A-B: healthy coronary vessel, C-D: atherosclerosis stage 3, E-F: atherosclerosis stage 5B. For all stages: Left, total MGP (mAb3-15); right, under-carboxylated MGP (mAb35-53).

FIG. 14 illustrates the immunohistochemical localization of various forms of MGP in coronary arteries during different stages of atherosclerosis. In healthy arteries (1A-1B), a narrow intima is seen, with no visible calcium precipitations. MGP total antigen (stained with anti-MGP[3-15]) accumulates around the elastin fibers; undercarboxylated MGP (stained with anti-MGP[35-53][Glu]) was not found at this stage, thus demonstrating that this vessel wall is sufficient in vitamin K. In stage 3 atherosclerosis (1C-1D), substantial intima thickening was observed with apparent vesicular accumulations of total MGP antigen. Similar patterns were found for under-carboxylated MGP, suggesting vitamin K-deficiency in these structures. In atherosclerosis stage 5b (calcium precipitates and bone formation) most of the total MGP antigen accumulated between the intimal tissue and calcified areas, and also here a substantial part was in the form of under-carboxylated MGP (1E-1F). Thus in all stages of atherosclerosis vitamin K-deficiency was demonstrated. This identifies atherosclerotic patients as a group who might benefit from vitamin K-supplements, which is of importance for public health and for the health food industry.

Hybridoma cell line B11A#1, which produces a monoclonal antibody directed against an epitope in human matrix Gla protein residues 35-49[Glu], was deposited on Mar. 23, 2004 with Deutsche Sammlung von Mikroorganizmen and Zeilkulturen GmbH (DSMZ) located at Mascheroder Weg 1b, D-38124 Braunschweig, Germany as accession number DSM ACC2639. Hybridoma cell line 52.1#1, which produces a monoclonal antibody directed against an epitope in human matrix Gla protein residues 3-15, was deposited on Mar. 23, 2004 with DSMZ, as accession number DSM ACC2638.

The present disclosure is to be considered as in all respects illustrative and not restrictive, the scope of the invention being indicated by the appended claims, and all changes which come within the meaning and range of equivalency are intended to be embraced therein.

The invention claimed is:

1. A diagnostic kit for assaying human matrix Gla protein in a serum sample, comprising:
   one or more monoclonal antibodies directed against an epitope in human matrix Gla protein residues 3-15, 35-49, or 35-53, alone or in combination with a monoclonal antibody directed against an epitope in human matrix Gla protein residues 61-79, or 54-84, or combinations thereof, wherein said one or more antibodies are produced by a hydridoma formed by fusion of cells from a mouse myeloma and spleen cells from a mouse previously immunized with a peptide homologous to human matrix Gla protein residues 3-15, 35-49, 35-53, or 61-79, or 54-84.

2. A monoclonal antibody of class IgG, comprising a monoclonal antibody directed against an epitope in human matrix Gla protein residues 35-53, wherein said antibody is produced by a hydridoma formed by fusion of cells from a mouse myeloma and spleen cells from a mouse previously immunized with a peptide homologous to human matrix Gla protein residues 35-53.

3. A hybridoma cell line B11A#1 deposited with Deutsche Sammlung von Mikroorganizmen and Zellkulturen GmbH (DSMZ) as accession number DSM ACC2639.

4. A hybridoma cell line 52.1#1 deposited with Deutsche Sammlung von Mikroorganizmen and Zellkulturen GmbH (DSMZ) as accession number DSM ACC2638.

5. A monoclonal antibody directed against an epitope in human matrix Gla protein, selected from the group consisting of epitopes in human matrix Gla protein residues 3-15, 35-49, and 35-53.

* * * * *

SEQUENCE LISTING

```
<160> NUMBER OF SEQ ID NOS: 4

<210> SEQ ID NO 1
<211> LENGTH: 891
<212> TYPE: DNA
<213> ORGANISM: Artificial Sequence
<220> FEATURE:
<223> OTHER INFORMATION: Synthetic construct containing 6-His tag -
      DHFR - linker (=4 amino acids) - MGP
<221> NAME/KEY: CDS
<222> LOCATION: (1)...(891)

<400> SEQUENCE: 1 atg aga gga tcg cat cac cat cac cat cac gga tcc ggc atc atg gtt      48
Met Arg Gly Ser His His His His His His Gly Ser Gly Ile Met Val
1               5                   10                  15 cga cca ttg aac tcg atc gtc gcc gtg tcc caa aat atg ggg att ggc      96
Arg Pro Leu Asn Ser Ile Val Ala Val Ser Gln Asn Met Gly Ile Gly
            20                  25                  30 aag aac gga gac cta ccc tgg cct ccg ctc agg aac gag ttc aag tac     144
Lys Asn Gly Asp Leu Pro Trp Pro Pro Leu Arg Asn Glu Phe Lys Tyr
```

```
ttc caa aga atg acc aca acc tct tca gtg gaa ggt aaa cag aat ctg      192
Phe Gln Arg Met Thr Thr Thr Ser Ser Val Glu Gly Lys Gln Asn Leu
     50                  55                  60 gtg att atg ggt agg aaa acc tgg ttc tcc att cct gag aag aat cga      240
Val Ile Met Gly Arg Lys Thr Trp Phe Ser Ile Pro Glu Lys Asn Arg
 65                  70                  75                  80 cct tta aag gac aga att aat ata gtt ctc agt aga gaa ctc aaa gaa      288
Pro Leu Lys Asp Arg Ile Asn Ile Val Leu Ser Arg Glu Leu Lys Glu
                 85                  90                  95 cca cca cga gga gct cat ttt ctt gcc aaa agt ttg gat gat gcc tta      336
Pro Pro Arg Gly Ala His Phe Leu Ala Lys Ser Leu Asp Asp Ala Leu
            100                 105                 110 aga ctt att gaa caa ccg gaa ttg gca agt aaa gta gac atg gtt tgg      384
Arg Leu Ile Glu Gln Pro Glu Leu Ala Ser Lys Val Asp Met Val Trp
        115                 120                 125 ata gtc gga ggc agt tct gtt tac cag gaa gcc atg aat caa cca ggc      432
Ile Val Gly Gly Ser Ser Val Tyr Gln Glu Ala Met Asn Gln Pro Gly
    130                 135                 140 cac ctt aga ctc ttt gtg aca agg atc atg cag gaa ttt gaa agt gac      480
His Leu Arg Leu Phe Val Thr Arg Ile Met Gln Glu Phe Glu Ser Asp
145                 150                 155                 160 acg ttt ttc cca gaa att gat ttg ggg aaa tat aaa ctt ctc cca gaa      528
Thr Phe Phe Pro Glu Ile Asp Leu Gly Lys Tyr Lys Leu Leu Pro Glu
                165                 170                 175 tac cca ggc gtc ctc tct gag gtc cag gag gaa aaa ggc atc aag tat      576
Tyr Pro Gly Val Leu Ser Glu Val Gln Glu Glu Lys Gly Ile Lys Tyr
            180                 185                 190 aag ttt gaa gtc tac gag aag aaa ggt tcc aga tct gca tgc att gaa      624
Lys Phe Glu Val Tyr Glu Lys Lys Gly Ser Arg Ser Ala Cys Ile Glu
        195                 200                 205 ggt cgt tat gaa tca cat gaa agc atg gaa tct tat gaa ctt aat ccc      672
Gly Arg Tyr Glu Ser His Glu Ser Met Glu Ser Tyr Glu Leu Asn Pro
    210                 215                 220 ttc att aac agg aga aat gca aat acc ttc ata tcc cct cag cag aga      720
Phe Ile Asn Arg Arg Asn Ala Asn Thr Phe Ile Ser Pro Gln Gln Arg
225                 230                 235                 240 tgg aga gct aaa gtc caa gag agg atc cga gaa cgc tct aag cct gtc      768
Trp Arg Ala Lys Val Gln Glu Arg Ile Arg Glu Arg Ser Lys Pro Val
                245                 250                 255 cac gag ctc aat agg gaa gcc tgt gat gac tac aga ctt tgc gaa cgc      816
His Glu Leu Asn Arg Glu Ala Cys Asp Asp Tyr Arg Leu Cys Glu Arg
            260                 265                 270 tac gcc atg gtt tat gga tac aat gct gcc tat aat cgc tac ttc agg      864
Tyr Ala Met Val Tyr Gly Tyr Asn Ala Ala Tyr Asn Arg Tyr Phe Arg
        275                 280                 285 aag cgc cga ggg gcc aaa aag ctt aat                                  891
Lys Arg Arg Gly Ala Lys Lys Leu Asn
    290                 295

<210> SEQ ID NO 2
<211> LENGTH: 297
<212> TYPE: PRT
<213> ORGANISM: Artificial Sequence
<220> FEATURE:
<223> OTHER INFORMATION: Protein encoded by Sequence 1 containing 6-His
      tag - DHFR - linker (=4 amino acids) - MGP

<400> SEQUENCE: 2

Met Arg Gly Ser His His His His His Gly Ser Gly Ile Met Val
 1               5                  10                  15
```

```
Arg Pro Leu Asn Ser Ile Val Ala Val Ser Gln Asn Met Gly Ile Gly
             20                  25                  30

Lys Asn Gly Asp Leu Pro Trp Pro Leu Arg Asn Glu Phe Lys Tyr
         35                  40                  45

Phe Gln Arg Met Thr Thr Thr Ser Ser Val Glu Gly Lys Gln Asn Leu
 50                  55                  60

Val Ile Met Gly Arg Lys Thr Trp Phe Ser Ile Pro Glu Lys Asn Arg
 65                  70                  75                  80

Pro Leu Lys Asp Arg Ile Asn Ile Val Leu Ser Arg Glu Leu Lys Glu
                 85                  90                  95

Pro Pro Arg Gly Ala His Phe Leu Ala Lys Ser Leu Asp Asp Ala Leu
            100                 105                 110

Arg Leu Ile Glu Gln Pro Glu Leu Ala Ser Lys Val Asp Met Val Trp
            115                 120                 125

Ile Val Gly Gly Ser Ser Val Tyr Gln Glu Ala Met Asn Gln Pro Gly
            130                 135                 140

His Leu Arg Leu Phe Val Thr Arg Ile Met Gln Glu Phe Glu Ser Asp
145                 150                 155                 160

Thr Phe Phe Pro Glu Ile Asp Leu Gly Lys Tyr Lys Leu Leu Pro Glu
                165                 170                 175

Tyr Pro Gly Val Leu Ser Glu Val Gln Glu Glu Lys Gly Ile Lys Tyr
            180                 185                 190

Lys Phe Glu Val Tyr Glu Lys Lys Gly Ser Arg Ser Ala Cys Ile Glu
            195                 200                 205

Gly Arg Tyr Glu Ser His Glu Ser Met Glu Ser Tyr Glu Leu Asn Pro
            210                 215                 220

Phe Ile Asn Arg Arg Asn Ala Asn Thr Phe Ile Ser Pro Gln Gln Arg
225                 230                 235                 240

Trp Arg Ala Lys Val Gln Glu Arg Ile Arg Glu Arg Ser Lys Pro Val
                245                 250                 255

His Glu Leu Asn Arg Glu Ala Cys Asp Asp Tyr Arg Leu Cys Glu Arg
            260                 265                 270

Tyr Ala Met Val Tyr Gly Tyr Asn Ala Ala Tyr Asn Arg Tyr Phe Arg
            275                 280                 285

Lys Arg Arg Gly Ala Lys Lys Leu Asn
            290                 295

<210> SEQ ID NO 3
<211> LENGTH: 39
<212> TYPE: DNA
<213> ORGANISM: Artificial Sequence
<220> FEATURE:
<223> OTHER INFORMATION: Synthetic Primer

<400> SEQUENCE: 3
tatgcatgca ttgaaggtcg ttatgaatca catgaaagc                          39

<210> SEQ ID NO 4
<211> LENGTH: 30
<212> TYPE: DNA
<213> ORGANISM: Artificial Sequence
<220> FEATURE:
<223> OTHER INFORMATION: Synthetic Primer

<400> SEQUENCE: 4
tataagcttt ttggcccctc ggcgcttcct                                    30
```